US012603184B2

(12) United States Patent
Morin

(10) Patent No.: US 12,603,184 B2
(45) Date of Patent: Apr. 14, 2026

(54) SYSTEMS AND METHODS FOR CONTINUOUS CANCER TREATMENT AND PROGNOSTICS

(71) Applicant: The Regents of the University of California, Oakland, CA (US)

(72) Inventor: Olivier Morin, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/557,909

(22) PCT Filed: May 2, 2022

(86) PCT No.: PCT/US2022/072068
§ 371 (c)(1),
(2) Date: Oct. 27, 2023

(87) PCT Pub. No.: WO2022/232850
PCT Pub. Date: Nov. 3, 2022

(65) Prior Publication Data
US 2024/0233952 A1 Jul. 11, 2024

Related U.S. Application Data

(60) Provisional application No. 63/182,718, filed on Apr. 30, 2021.

(51) Int. Cl.
*G16H 50/20* (2018.01)
*G06F 40/216* (2020.01)
(Continued)

(52) U.S. Cl.
CPC .......... *G16H 50/30* (2018.01); *G06F 40/216* (2020.01); *G16H 10/60* (2018.01); *G16H 50/20* (2018.01); *G16H 50/70* (2018.01)

(58) Field of Classification Search
CPC ........ G16H 50/30; G16H 10/60; G16H 50/70; G16H 50/20; G06F 40/216
See application file for complete search history.

(56) References Cited

U.S. PATENT DOCUMENTS

2015/0154367 A1* 6/2015 Shetty ................... G16H 50/20
705/2
2018/0038866 A1 2/2018 Paik
(Continued)

FOREIGN PATENT DOCUMENTS

WO 2020006495 A1 1/2020
WO 2022232850 A1 11/2022

OTHER PUBLICATIONS

Lee E, Jung SY, Hwang HJ, Jung J Patient-Level Cancer Prediction Models From a Nationwide Patient Cohort: Model Development and Validation JMIR Med Inform 2021; (Year: 2021).*
(Continued)

*Primary Examiner* — Matthew L Hamilton
(74) *Attorney, Agent, or Firm* — KPPB LLP

(57) ABSTRACT

Oncology faces a digital chasm in its quest for personalized treatments. Despite the adoption of electronic health records (EHR), most hospitals are ill-equipped for data science research. Embodiments herein describe a continuously learning infrastructure through which multimodal health data are systematically organized and data quality is assessed with the goal of applying artificial intelligence to address unmet clinical needs. Embodiments describe systems and methods for improved cancer prognostics, including by obtaining electronic medical records and performing natural language processing thereon. Additional embodiments apply term frequency inverse document frequency to identify terms that are predictive for cancer survival. Additional embodiments are capable of performing in silico
(Continued)

Obtain Initial Medical Data — 502

Perform NLP on Medical Data — 504

Apply Machine Learning Model — 506

Treat Individual — 508

500 clinical trials based on information comprised in a collection of health records.

17 Claims, 27 Drawing Sheets

(51) Int. Cl.
| | |
|---|---|
| *G16H 10/60* | (2018.01) |
| *G16H 50/30* | (2018.01) |
| *G16H 50/70* | (2018.01) |

(56) References Cited

U.S. PATENT DOCUMENTS

| | | | | |
|---|---|---|---|---|
| 2018/0322254 | A1 | 11/2018 | Smurro | |
| 2020/0175203 | A1* | 6/2020 | Allen | G16H 10/60 |
| 2020/0272919 | A1* | 8/2020 | Haimson | G16H 50/20 |
| 2022/0044812 | A1* | 2/2022 | Barnes | G16H 50/20 |
| 2022/0068443 | A1* | 3/2022 | Ransom | G16H 10/20 |
| 2023/0074363 | A1* | 3/2023 | Yang | G16H 50/20 |

OTHER PUBLICATIONS

International Preliminary Report on Patentability for International Application PCT/US2022/072068, Report issued Oct. 24, 2023, Mailed on Nov. 9, 2023, 06 pgs.

International Search Report and Written Opinion for International Application No. PCT/US2022/072068, Search completed Jun. 29, 2022, Mailed Jul. 19, 2022, 11 pgs.

Aizawa, "An information-theoretic perspective of tf-idf measures", Information Processing and Management, vol. 39, No. 1, Jan. 2003, pp. 45-65, doi: 10.1016/S0306-4573(02)00021-3.

Banerjee et al., "Natural Language Processing Approaches to Detect the Timeline of Metastatic Recurrence of Breast Cancer", JCO Clinical Cancer Informatics, vol. 3, Oct. 4, 2019, 12 pgs., doi: 10.1200/CCI.19.00034.

Frost et al., "Using the Electronic Medical Record to Identify Patients at High Risk for Frequent Emergency Department Visits and High System Costs", The American Journal of Medicine, vol. 130, No. 5, May 2017, pp. 601.e17-601.e22, doi: 10.1016/j.amjmed.2016.12.008.

Hong et al., "Predicting Emergency Visits and Hospital Admissions During Radiation and Chemoradiation: An Internally Validated Pretreatment Machine Learning Algorithm", JCO Clinical Cancer Informatics, vol. 2, Aug. 30, 2018, 11 pgs., doi: 10.1200/CCI.18.00037.

Jackson, "Building the 'continuous learning' healthcare system", Health Information Management Journal, vol. 43, No. 1, Mar. 2014, pp. 4-5, doi: 10.1177/183335831404300101.

Kann et al., "Pretreatment Identification of Head and Neck Cancer Nodal Metastasis and Extranodal Extension Using Deep Learning Neural Networks", Scientific Reports, vol. 8, Article 14036, Sep. 2018, 11 pgs., doi: 10.1038/s41598-018-32441-y.

Lin et al., "Deep Learning for Automated Contouring of Primary Tumor Volumes by MRI for Nasopharyngeal Carcinoma", Radiology, vol. 291, No. 3, Jun. 2019, pp. 677-686, doi: 10.1148/radiol.2019182012.

Liu et al., "MR-based treatment planning in radiation therapy using a deep learning approach", Journal of Applied Clinical Medical Physics, vol. 20, No. 3, Mar. 2019, pp. 105-114, doi: 10.1002/acm2.12554.

Morin et al., "MEDomics: A Framework For Artificial Intelligence In Radiation Oncology", Astro News, 2019, 4 pgs.

Norgeot et al., "A call for deep-learning healthcare", Nature Medicine, vol. 25, Jan. 2019, pp. 14-15, doi: 10.1038/s41591-018-0320-3.

Phillips et al., "Assessment of Accuracy of an Artificial Intelligence Algorithm to Detect Melanoma in Images of Skin Lesions", JAMA Network Open, vol. 2, No. 10, Article e1913436, Oct. 16, 2019, pp. 1-12, doi: 10.1001/jamanetworkopen.2019.13436.

Rodriguez-Ruiz et al., "Stand-Alone Artificial Intelligence for Breast Cancer Detection in Mammography: Comparison With 101 Radiologists", Journal of the National Cancer Institute, vol. 111, No. 9, Mar. 5, 2019, pp. 916-922, doi: 10.1093/jnci/djy222.

Zwanenburg et al., "The Image Biomarker Standardization Initiative: Standardized Quantitative Radiomics for High-Throughput Image-based Phenotyping", Radiology, vol. 295, No. 2, May 2020, pp. 328-338, doi: 10.1148/radiol.2020191145.

* cited by examiner

Obtain Initial Medical Data — 502

Perform NLP on Medical Data — 504

Apply Machine Learning Model — 506

Treat Individual — 508

500

SYSTEMS AND METHODS FOR CONTINUOUS CANCER TREATMENT AND PROGNOSTICS

CROSS REFERENCE TO RELATED APPLICATIONS

This application is a national stage of PCT Application Ser. No. PCT/US2022/072068, entitled "Systems and Methods for Continuous Cancer Treatment and Prognostics" to Olivier Morin, filed May 2, 2022, which claims priority to U.S. Provisional Application Ser. No. 63/182,718, entitled "Systems and Methods for Continuous Cancer Treatment and Prognostics" to Olivier Morin, filed Apr. 30, 2021, the disclosures of which are herein incorporated by reference in their entireties.

FIELD OF THE INVENTION

The present disclosure is directed to cancer treatment and prognostics; and more particularly to systems and methods comprising artificial intelligence or machine learning capabilities to continuously assess electronic health information for improved treatment and prognostic efficacy.

BACKGROUND OF THE INVENTION

Oncology faces a digital chasm in its quest for personalized treatments. Modern health systems generate and store enormous amounts of digital patient information, which holds significant potential to personalize and improve the delivery of medical care. In recent years, adoption of comprehensive electronic health records (EHR) systems and advances in machine learning (ML) and artificial intelligence (AI) have led to numerous promising and potentially clinically applicable examples supporting the utility of harnessing this growing pool of digital data.

The fragmented information systems across the different disciplines of oncology present one of the most significant challenges to further AI advances in clinical oncology. While the cost associated with collecting and maintaining diverse oncology data has decreased tremendously in large part through the increased adoption of comprehensive EHRs, the vast majority of hospitals and clinics are ill-equipped to process diverse siloed oncology data in a meaningful way, including toward human augmentation for imaging, dermatology, pathology, endoscopy, and fundoscopy, and toward the development of clinically relevant algorithms for the prediction of acute organ injury, infection, intensive care admission, and emergency department visits.

Past attempts at AI or ML for oncology have been modest. Hong et al utilized an institutional EHR data warehouse to extract structured clinical variables for creation of a ML model to predict emergency department visits among oncology patients. (See e.g., Hong, J. C., et al. Predicting Emergency Visits and Hospital Admissions During Radiation and Chemoradiation: An Internally Validated Pretreatment Machine Learning Algorithm. JCO Clin Cancer Inform 2, 1-11 (2018); the disclosure of which is hereby incorporated by reference in its entirety.) Additional groups have focused on imaging, demonstrating improved detection of melanoma, breast cancer, and extranodal extension in head and neck cancer, as well as automation of tumor and organ-at-risk delineation and dosimetry in planning of radiation therapy. (See e.g., Phillips, M., et al. Assessment of Accuracy of an Artificial Intelligence Algorithm to Detect Melanoma in Images of Skin Lesions. JAMA Netw Open 2, e1913436 (2019); Rodriguez-Ruiz, A., et al. Stand-Alone Artificial Intelligence for Breast Cancer Detection in Mammography: Comparison With 101 Radiologists. J Natl Cancer Inst 111, 916-922 (2019); Kann, B. H., et al. Pretreatment Identification of Head and Neck Cancer Nodal Metastasis and Extranodal Extension Using Deep Learning Neural Networks. Sci Rep 8, 14036 (2018); Lin, L., et al. Deep Learning for Automated Contouring of Primary Tumor Volumes by MRI for Nasopharyngeal Carcinoma. Radiology 291, 677-686 (2019); and Liu, F., et al. MR-based treatment planning in radiation therapy using a deep learning approach; the disclosures of which are hereby incorporated by reference in their entireties.) Others still have focused on extracting clinical information and prognosis from unstructured medical notes. (See e.g., Banerjee, I., et al. Natural Language Processing Approaches to Detect the Timeline of Metastatic Recurrence of Breast Cancer. JCO Clin Cancer Inform 3, 1-12 (2019); the disclosure of which is hereby incorporated by reference in its entirety.) However, the limited modalities of these systems have failed to deliver clinically actionable results.

SUMMARY OF THE INVENTION

The present disclosure provides, in accordance with the current invention, embodiments of systems and methods for continuous cancer treatment and prognostics.

In some aspects, the techniques described herein relate to a method for determining cancer prognosis, including obtaining medical data for an individual, where the medical data includes a cancer diagnosis and physician notes, performing natural language processing (NLP) on the medical data, and applying a machine learning model on the natural language processed medical data to determine a prognostic for the individual.

In some aspects, the techniques described herein relate to a method, where the machine learning model identifies a treatment option for the individual, where the treatment increases the prognostic for the individual.

In some aspects, the techniques described herein relate to a method, further including treating the individual with the identified treatment to increase the prognostic for the individual.

In some aspects, the techniques described herein relate to a method, where the treatment is selected from immunotherapy, targeted therapy, radiation therapy, chemotherapy, and surgical intervention.

In some aspects, the techniques described herein relate to a method, further including updating the medical data for the individual.

In some aspects, the techniques described herein relate to a method, further including performing NLP on the updated medical data and re-applying the machine learning model on the updated natural language processed medical data to update the prognostic for the individual.

In some aspects, the techniques described herein relate to a method, where the machine learning model is trained by obtaining a collection of medical records from a medical institution, where each record in the collection of medical records includes data for an individual diagnosed with cancer, processing the collection of medical records, and performing NLP on the collection of medical records.

In some aspects, the techniques described herein relate to a method, where the processing step includes de-identifying the collection of medical records.

In some aspects, the techniques described herein relate to a method, where the processing step includes separating the records for a single cancer type.

In some aspects, the techniques described herein relate to a method, further including selecting complete records in the collection of medical records.

In some aspects, the techniques described herein relate to a method, where the machine learning model is selected from a Support Vector Machine (SVM), a Random Forest (RF), a Classification and Regression Tree (CART), a logistic regression with elastic net regularization (GLMNET), a least absolute shrinkage and selection operator (LASSO), and a Gradient Boosting Machines (GBM).

In some aspects, the techniques described herein relate to a method, where performing NLP includes applying term frequency inverse document frequency to the medical data.

In some aspects, the techniques described herein relate to a system for determining a cancer prognosis for an individual, including a central computing system configured to receive electronic health records from a medical institution, where the central computing system includes a machine learning model trained to determine a prognostic for an individual.

In some aspects, the techniques described herein relate to a system, where the machine learning model is trained by obtaining a collection of medical records from the medical institution, where each record in the collection of medical records includes data for an individual diagnosed with cancer, processing the collection of medical records, and performing natural language processing (NLP) on the collection of medical records.

In some aspects, the techniques described herein relate to a system, where the processing step includes de-identifying the collection of medical records.

In some aspects, the techniques described herein relate to a system, where the processing step includes separating the records for a single cancer type.

In some aspects, the techniques described herein relate to a system, further including selecting complete records in the collection of medical records.

In some aspects, the techniques described herein relate to a system, where performing NLP includes applying term frequency inverse document frequency to the medical data.

In some aspects, the techniques described herein relate to a system, where the central computing system is configured to receive electronic health records from a plurality of medical institutions.

In some aspects, the techniques described herein relate to a system, where the central computing is configured to receive the electronic health records via a network.

BRIEF DESCRIPTION OF THE DRAWINGS

The description will be more fully understood with reference to the following figures and data, which are presented as exemplary embodiments of the disclosure and should not be construed as a complete recitation of the scope of the invention, wherein:

FIG. 3A: Distribution of number of days per month with at least 1 medical entry for breast cancer patients for a time period of 6 months prior to initial diagnosis until 24 months past diagnosis. The box plots indicate the median, first/third quartiles and the minimum and maximum values over the entire breast patient population. FIG. 3B: Left—Distribution of the breast patient total number of days with medical entries for the time period in A as a function of the computed temporal continuity score of medical entries. Right—Close-up on a subset of the data represented on the left as identified by the dotted line. Circles/Dots—represents patients that received near full care at the institution, Xs—indicate patients that received partial care at the institution. The patient density for these two patient categories is plotted on the outside for the plotted range of medical entry volume and continuity score. The patient selection for statistical learning can be based on the cancer registry label and/or by using a quantile value for the distribution of entry volume and continuity score. FIG. 3C: Representation of the feature completeness for the selected breast patients (patient cohort identified by circles/dots) in B.

FIG. 4A.) Patient survival divided by staging groups: blue—stage 0-2, black—stage 3 and red—stage 4, Colors for staging are repeated in panels B-D., FIG. 4B. Patient survival (stage 4 only) for patients that were prescribed targeted drug (breast) and immunotherapy drugs (lung). FIG. 4C. Patient survival stratified by stage and for a computed Framingham risk score threshold of 0.3 (breast) and 0.43 (lung). FIG. 4D. Patient survival stratified by stage for patients with current or previous history of tobacco usage.

FIG. 6A. Comparison of statistical learning algorithms (least absolute shrinkage and selection operator—LASSO, gradient boosting machines—GBM, penalized Cox regression—pCox, Classification and Regression Tree—CART, support vector machine—SVM, random forest—RF) performance (area under the receiver operating curve for cross-validation and independent testing) for the binary prediction of breast (5 years) and lung (2 years) patient survival. Inspection of variable importance from out-of-bag penalty using the random forest classifier. FIG. 6B. Comparison of classifier performance with receiver-operator curves and area under the curve (AUC) scores. FIG. 6C. Kaplan-Meier survival plots obtained from 4 quartile strata using the random forest classifier on the holdout test sets for breast and lung cancer.

FIG. 14A. Comparison of statistical learning algorithms (least absolute shrinkage and selection operator—LASSO, gradient boosting machines—GBM, Classification and Regression Tree—CART, support vector machine—SVM, random forest—RF) performance (area under the receiver operating curve for cross-validation and independent testing) for the binary prediction of breast (5 years) and lung (2 years) patient survival. Inspection of variable importance from out-of-bag penalty using the random forest classifier. FIG. 14B. Comparison of classifier performance with receiver-operator curves and area under the curve (AUC) scores. FIG. 14C. Kaplan-Meier survival plots obtained from 4 quartile strata using the random forest classifier on the holdout test sets for breast and lung cancer.

DETAILED DESCRIPTION OF THE INVENTION

Figure 1A:
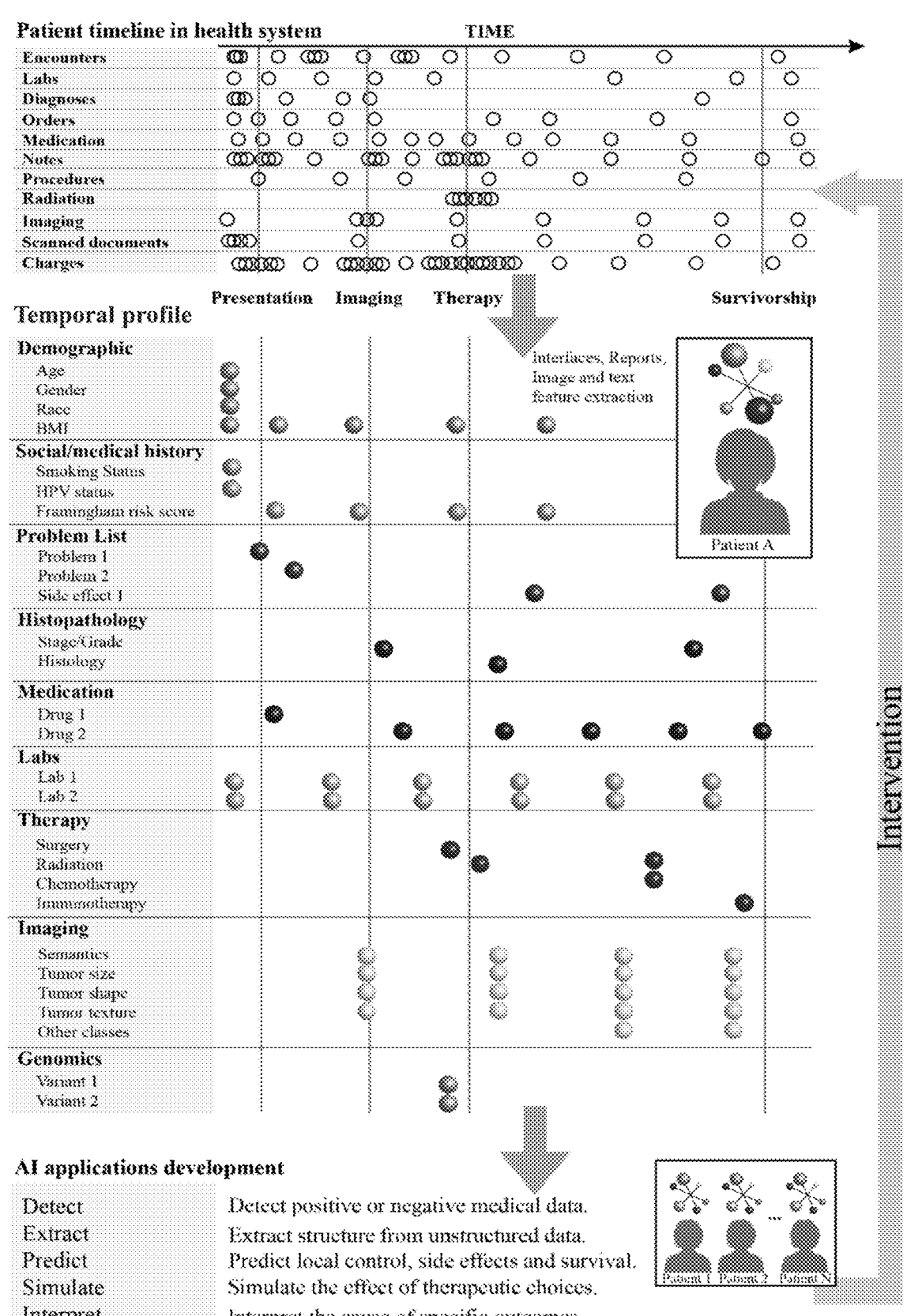
FIG. 1A illustrates an exemplary set of electronic health data records (encounters, labs, diagnoses, orders, medication, notes, procedures, radiation, imaging, scanned documents and financial charges) for a breast patient timeline through typical cancer management in accordance with various embodiments.

Turning to the drawings, many embodiments herein describe a continuously learning infrastructure through which multimodal health data are systematically organized and data quality is assessed with the goal of applying artificial intelligence to address unmet clinical needs. Using this framework, which can comprise thousands of cancer patients and millions of data points, numerous embodiments are capable of exploring prognostic factors for oncologic disease. Certain embodiments identify one or more risk scores that are robustly associated with mortality among both early-stage and advanced-stage cancer patients, a potentially actionable finding from a real-world cohort of oncology patients. Further, many embodiments use natural language processing of medical notes to continuously update estimates of prognosis as a given patient's disease course unfolds.

An overarching long-term hypothesis of AI development in oncology is that solutions able to create longitudinal real-time, patient-specific knowledge will improve quality of life and save lives. To this end, many embodiments detail a secure, comprehensive, dynamic, and expandable infrastructure designed to continuously capture multimodal electronic health information across a large and complex healthcare network. Numerous embodiments utilize this data infrastructure to examine system-wide care patterns and patient outcomes and to generate prognostic models with a focus on oncology. Certain embodiments are able to recapitulate known relationships between clinical predictors and overall survival, and some embodiments perform in-silico testing of clinical hypotheses in high-quality subsets of patients identified through automated processes. Further, many embodiments are capable of updating and improving a prognostic model over time, as a patient's illness unfolds, based on a longitudinal approach to natural language processing (NLP) of unstructured medical notes. Ultimately, embodiments combining structured and unstructured multimodal health information in a longitudinal context can facilitate the development of truly predictive and dynamic AI applications in oncology that will improve the quality and duration of patients' lives.

Structure of Machine Learning Models

Since most EHR notes compromise heterogeneous structures with extensive lengths, covering rich information, including (but not limited to) reports of radiology, pathology, medical oncology, radiation oncology, and discharge summary, many embodiments involve processing vast amounts of unstructured medical text. In order to capitalize on such a large volume of information, various embodiments incorporate a natural language processing (NLP) methodology using term frequency inverse document frequency (TF-IDF) to predict patient survival. Certain embodiments utilize a minimum number of medical records for an individual for initial prognostic analysis. Additional embodiments continually incorporate additional medical and/or physician records into for ongoing prognostic analysis, as a patient's illness unfolds.

Turning to FIG. 1A, a schematic of a patient specific profile in accordance with various embodiment is illustrated. In particular, as time progresses for an individual patient (e.g., from presentation of symptoms, imaging, therapy, etc.), medical records are updated and incorporated into a temporal profile for a patient (e.g., an individual patient profile with different events or records attached to a time-point in the course of care), such that the medical records include results from diagnostic tests, therapies, medications, imaging results, demographic information, medical notes. These separately generated temporal profiles form a comprehensive temporal representation of important elements of oncology used for the creation of medical informatics tools and AI applications, in accordance with various embodiments. Significant components of each profile include processed structured elements for common demographics, medical history, family medical history, diagnoses, laboratory results, medications, therapies received, imaging received, tumor size/shape, tumor texture, lymph node involvement, presence of metastatic disease, molecular subtypes, radiology annotations, pathology annotations, side effects, possible molecular tissue analyses, and diverse treatment outcomes. All data elements attached to the profile are stored with a category, name, value, and date. The data structure enables feature temporal changes to be captured and monitored.

Figure 1B:
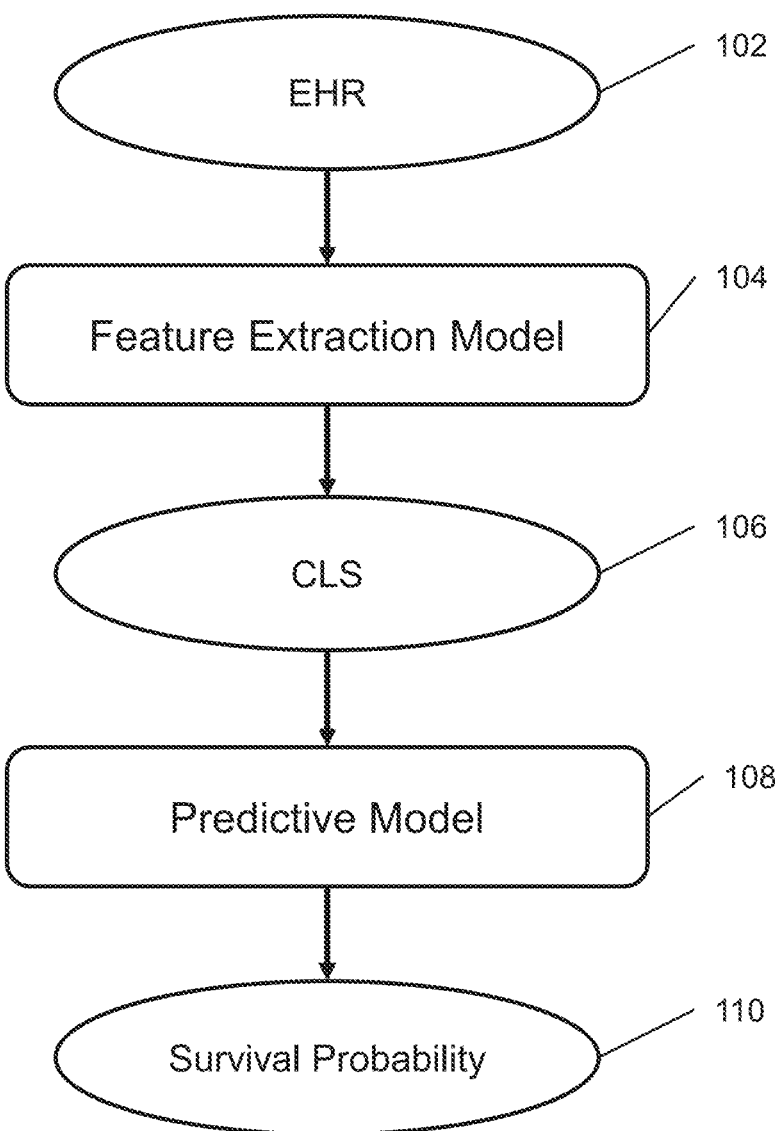
FIG. 1B illustrates an exemplary schematic of a machine learning model for cancer prognostics in accordance with various embodiments.

Turning to FIG. 1B, an exemplary schematic 100 of a machine learning model used in some embodiments is illustrated. Certain embodiments utilize a two-component model architecture for feature extraction and classification. The first model in some embodiments is a feature extraction model 104. The feature extraction model 104 of some embodiments breaks EHR notes 102 into sub-word units, or tokens. In such embodiments, each unit, or token, comprises one or more of the following: a) a token embedding; b) a segment embedding, which identifies the sequence that token embedding associates with; and c) positional embedding, which is composed of learned parameters identifying the position of the token in the input notes. In several embodiments, the tokens are concatenated. A feature extraction model 104 used in various embodiments, bins predictions provided by each subsequence within the concatenations. In many embodiments, the output of the feature extraction model 104 is conditional latent space (CLS) 106 extracted as a multi-dimensional vector from the final hidden layer of the feature extraction model 104. In various embodiments, the multi-dimensional vector is a 50-dimension vector, a 100-dimension vector, a 150-dimension vector, a 200-dimension vector, a 250-dimension vector, a 300-dimension vector, a 350-dimension vector, a 400-dimension vector, a 450-dimension vector, a 500-dimension vector, a 550-dimension vector, a 600-dimension vector, a 650-dimension vector, a 700-dimension vector, a 750-dimension vector, a 768-dimension vector, an 800-dimension vector, an 850-dimension vector, a 900-dimension vector, a 950-dimension vector, a 1000-dimension vector, or greater dimension vector. In various embodiments, the feature extraction model 104 is a Bidirectional Encoder Representatations from Transformers (BERT) model, while additional embodiments utilize one or more other models for NLP and feature extraction from EHR.

Further embodiments include a predictive model 108 using CLS 106 as input to classify survival probability 110. Various embodiments utilize one or more of the following for classification: Logistical Regression (LR), Support Vector Machine (SVM), Random Forest (RF), Classification and Regression Tree (CART), logistic regression with elastic net regularization (GLMNET), least absolute shrinkage and selection operator (LASSO), and Gradient Boosting Machines (GBM). The predictive model outputs a survival probability 110 based on the features extracted by the feature extraction model 104.

Figure 2:
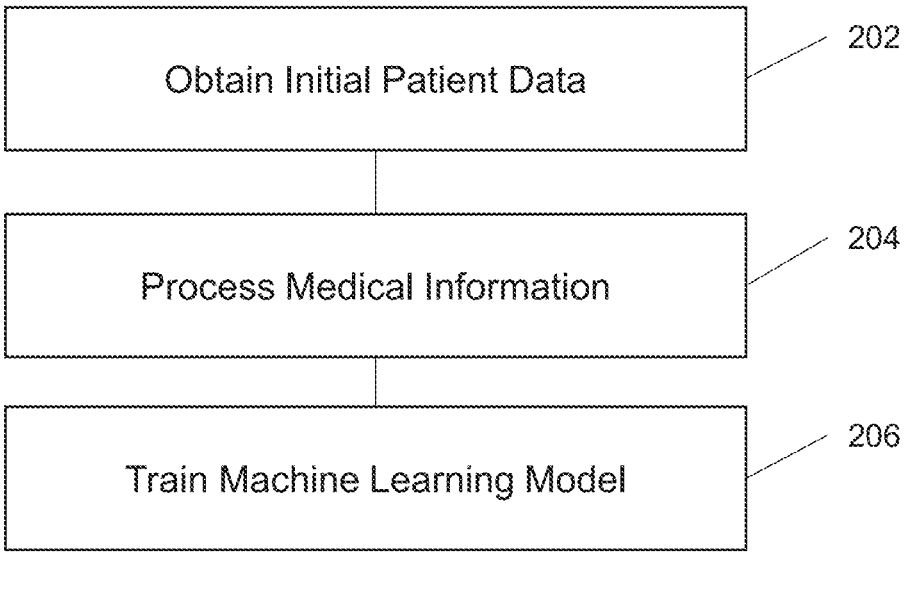
FIG. 2 illustrates an exemplary method to train a machine learning model for cancer prognostics in accordance with various embodiments.

Turning to FIG. 2, a method 200 to train a machine learning model for cancer prognostics in accordance with many embodiments is illustrated. At 202, many embodiments obtain initial patient data. When obtaining initial patient data, certain data may be incomplete for an individual, such as when the individual obtains partial care at an institution or requests a second opinion from an institution. Thus, certain embodiments utilize inclusion criteria to select for complete records. Some embodiments identify a maximum number of days of with different medical entry types (e.g., medical notes, encounters, labs, etc.).

Figure 3A:
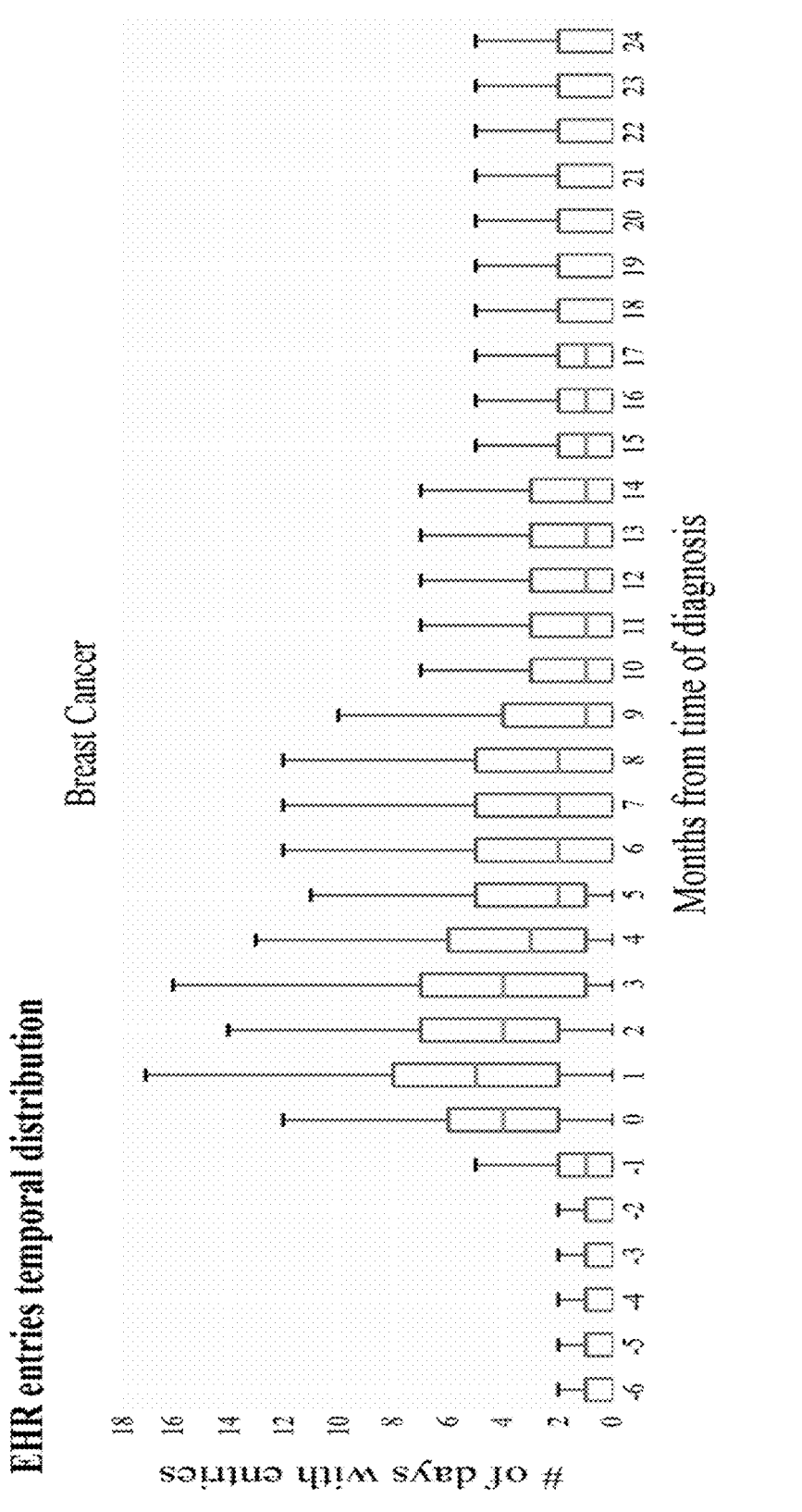
FIGS. 3A-3C illustrate an exemplary distribution of medical entries for breast patient population, patient selection and completeness of medical features used for statistical learning in accordance with various embodiments.
Figure 3B:
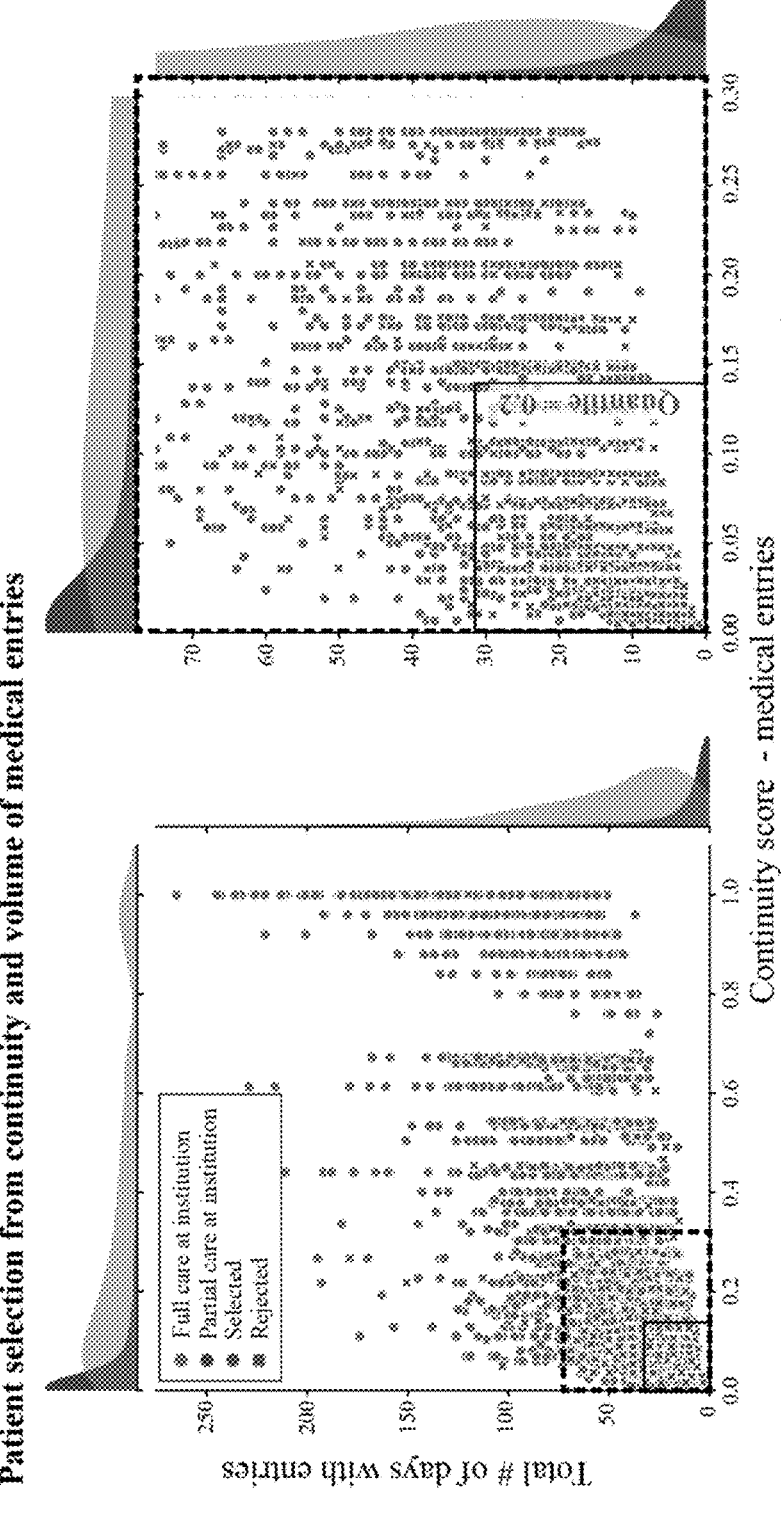
Figure 3C:
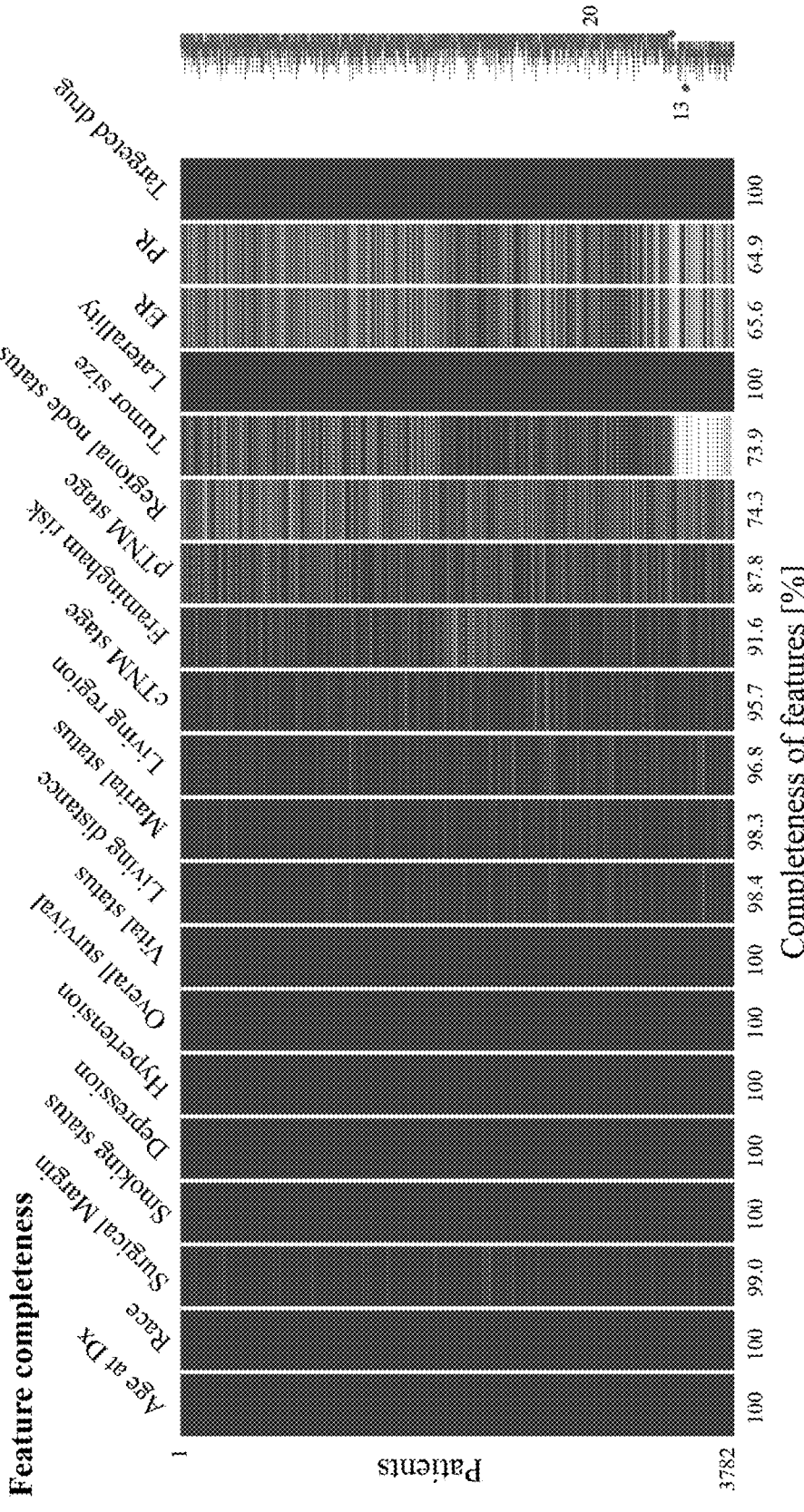

FIG. 3A illustrates exemplary EHR data of certain embodiments where the maximum number of entries ranges from 2-8 for the first 1-2 months post-diagnosis then gradually decreases over 2 years. Further embodiments determine a penalized continuity score and total number of days with entries to select for individuals or patients who received complete care at an institution. FIG. 3B illustrates an exemplary plot of the total number of days with entries as a function of the continuity score, where the left panel represents a full dataset, and the right panel represents an enlarged version of the dashed box area of the left panel. In the exemplary embodiment, selected individuals are represented by circles, while excluded individuals represented by Xs. FIG. 3C illustrates completeness of features of individuals selected for inclusion into an exemplary embodiment.

Returning to FIG. 2, at 204, many embodiments process medical information and/or records for machine learning. In many embodiments, individual reports are de-identified and compiled into a central system for machine learning. In many embodiments, profiles are dynamically generated and updated in a computation platform using one or more of the following methods:

1. Custom daily reports are generated from the EHR (Epic/Clarity relational database), the oncology information system (MOSAIQ, Elekta) and the regional cancer registry. These are transferred periodically (e.g., every 24 hours) to a central server. In certain embodiments, the transfer is conducted via secured interfaces (HL7) and comma-separated value (CSV) reports.

2. Natural language processing (NLP) classification methods are applied to medical, radiology, radiation oncology and pathology notes to extract additional features (smoking status, staging, histology, etc.) for the profile. In certain embodiments, the NLP method consists of a mix of semantic searches and application of deep learning implementation which were previously trained on user-defined labels.

3. Quantitative imaging methods are applied to MRI, PET and CT images using standardized image processing and feature extraction. (See e.g., Zwanenburg, A., et al. The Image Biomarker Standardization Initiative: Standardized Quantitative Radiomics for High-Throughput Image-based Phenotyping. Radiology, 191145 (2020); the disclosure of which is hereby incorporated by reference in its entirety.)

Various embodiments follow a hierarchy of programming classes: project, cohort, patient, and "MEDomics" which consists of a time-dependent profile of structured elements as well medical image and medical text objects. In certain embodiments, type of cancer or tumor (including, but not limited to, breast, glioma, lung, prostate) is separated and used in an individual model.

NLP on physician notes, in accordance with many embodiments, includes one or more of regular notes, narrative notes from radiology reports, impression notes from radiology reports, impression notes from pathology reports, and/or any other relevant notes. Many of these notes are unstructured, such that they do not have similar patterns or an underlying pattern or structure to notes. Thus, unstructured notes can be highly variable depending on the physician or other medical personnel making such notes. In various embodiments, notes are de-identified to remove protected health information and/or possible institutional biases. Further embodiments apply term frequency inverse document frequency (TF-IDF) to identify key specific terms that may identify or predict cancer survivability. (See e.g., Aizawa, A. An information-theoretic perspective of tf-idf measures. Information Processing & Management 39, 45-65 (2003); the disclosure of which is hereby incorporated by reference in its entirety.) Table 1 provides a list of data tables, elements and their utility for AI development.

At 206, various embodiments train a machine learning model based on the terms identified by the NLP. Machine learning models used in various embodiments include models capable of being trained with NLP data. For example, various embodiments use one or more of Support Vector Machine (SVM), Random Forest (RF), Classification and Regression Tree (CART), logistic regression with elastic net regularization (GLMNET), least absolute shrinkage and selection operator (LASSO), and Gradient Boosting Machines (GBM). Additional embodiments train the model using masking and/or next-sentence prediction tasks utilizing large-scale intensity care notes.

In Silico Clinical Trials

Figure 4A:
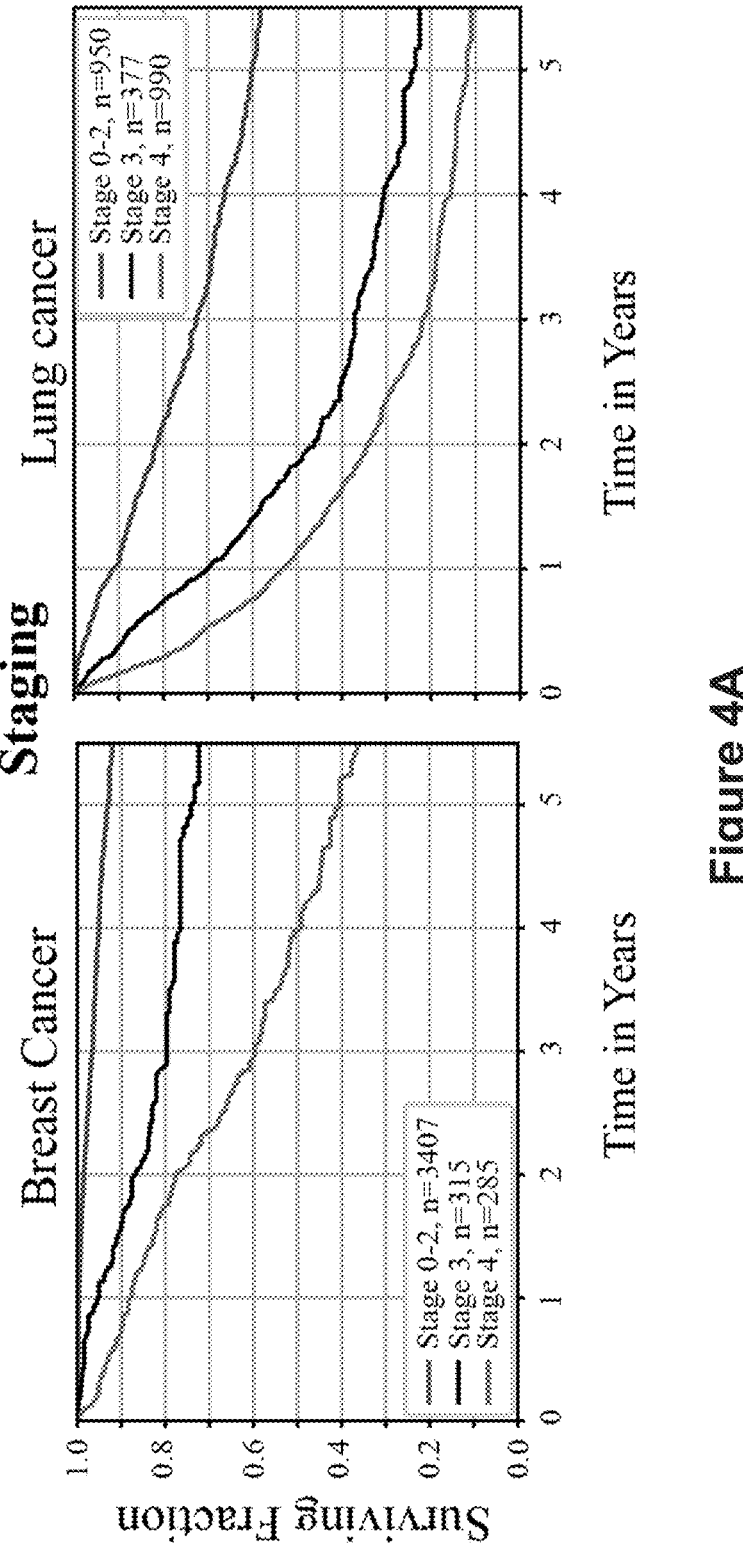
FIGS. 4A-4D illustrate exemplary Kaplan-Meier survival plots on selected breast and lung cancer patients in accordance with various embodiments. Survival plots for selected breast (left) and lung (right) patients from time of initial diagnosis.
Figure 4B:
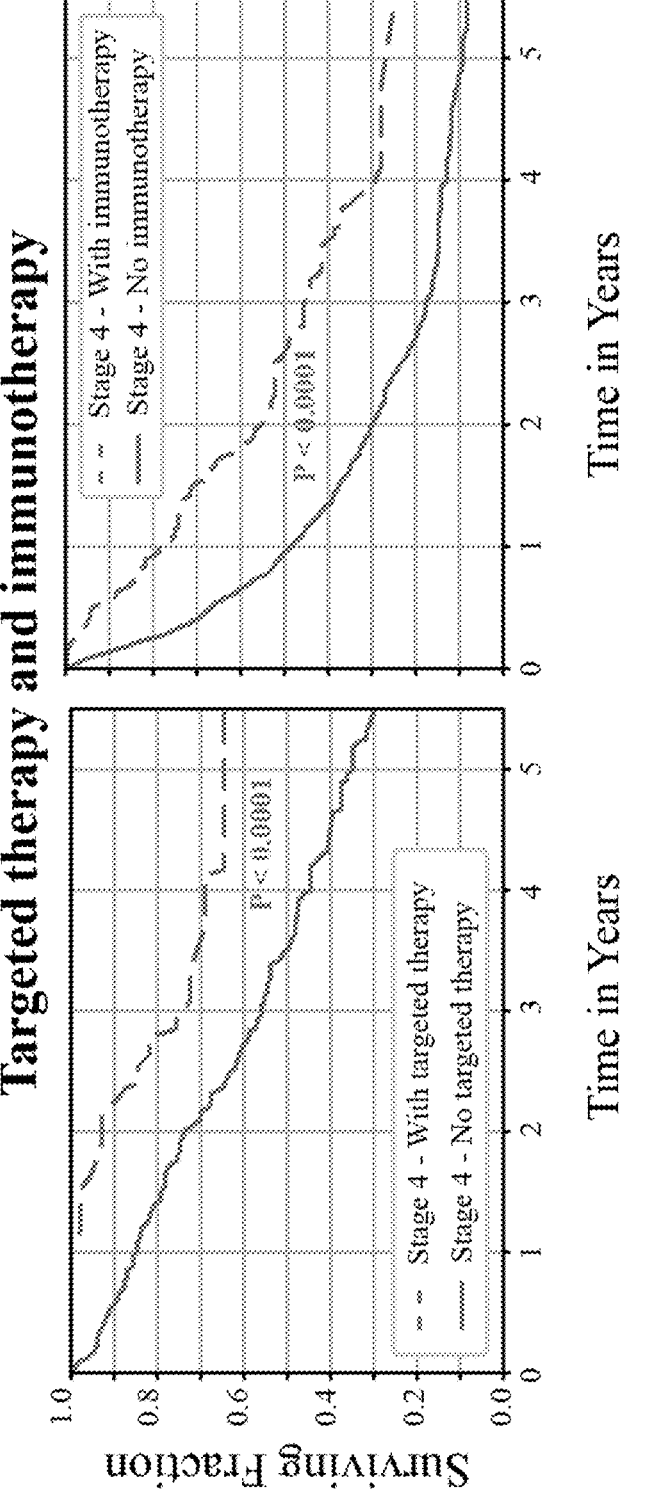
Figure 4C:
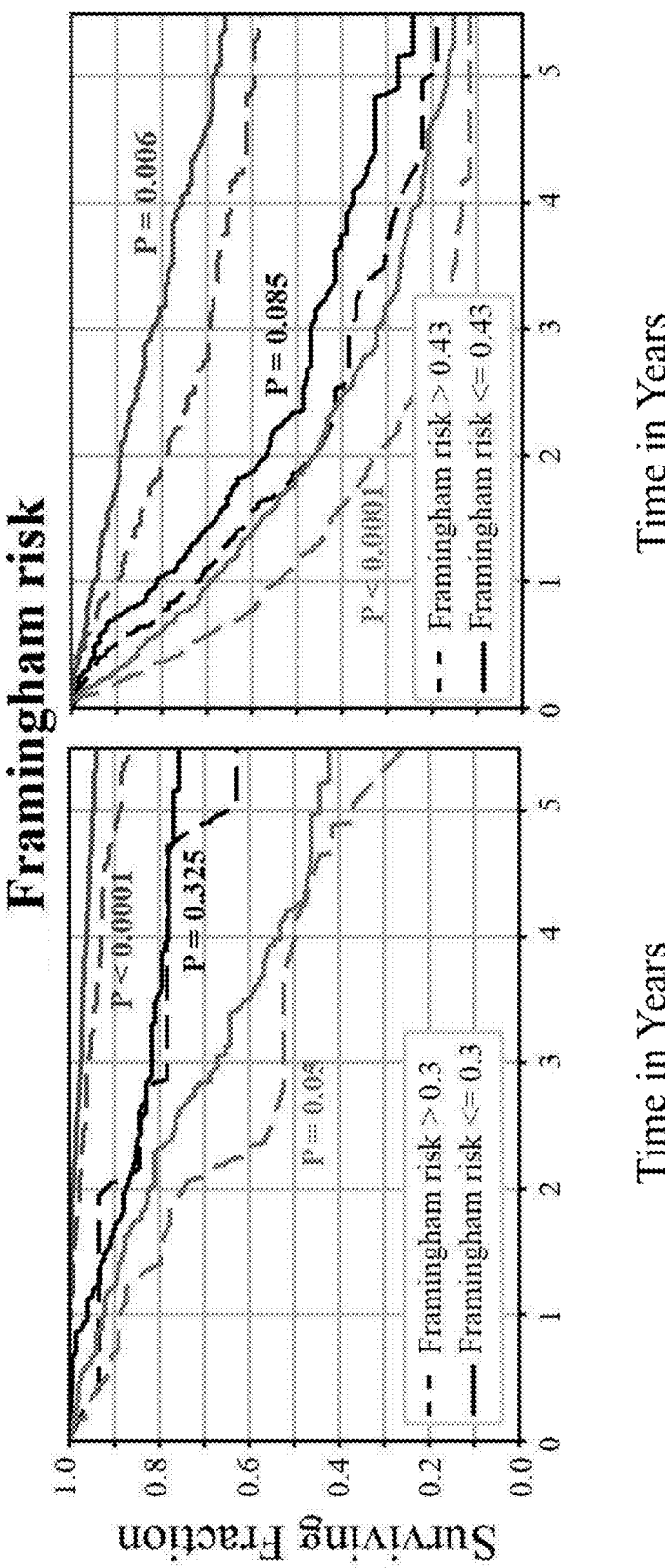
Figure 4D:
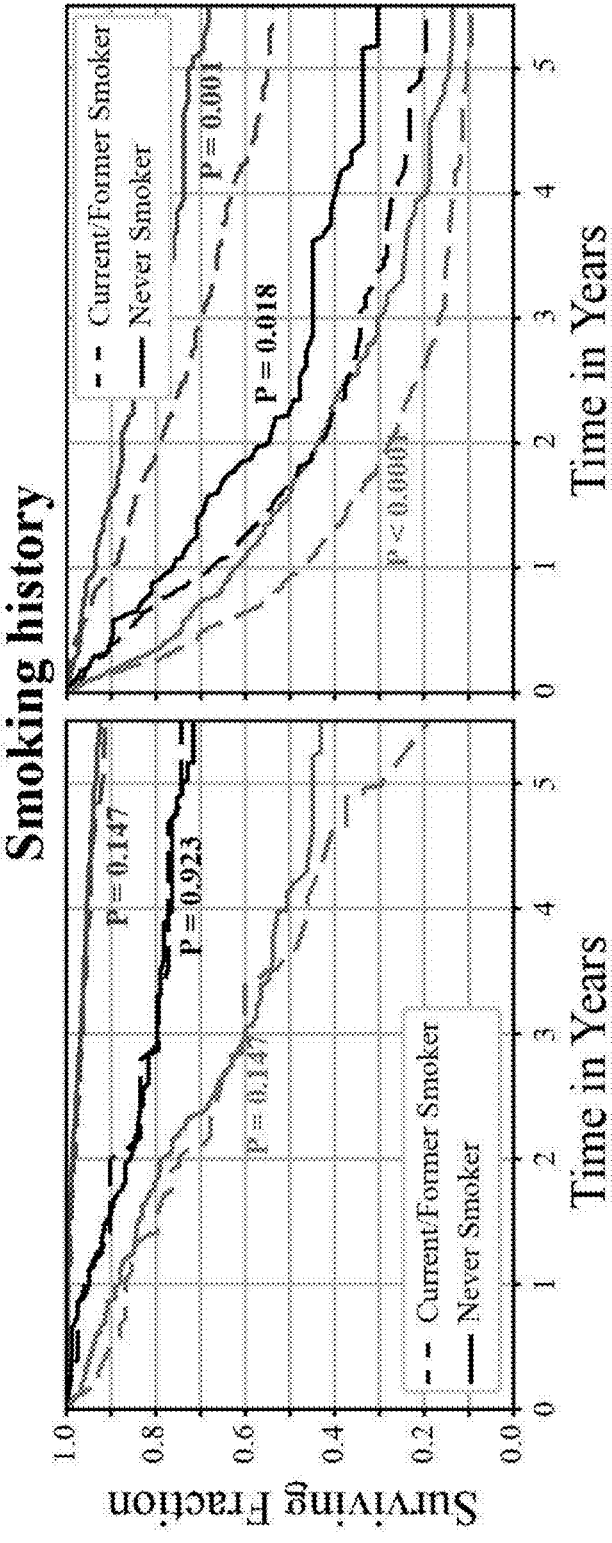

Many embodiments are capable of performing in silico clinical trials based on clinical variables and outcome. Exemplary data of some trials are illustrated in FIGS. 4A-4D, which illustrate exemplary survival outcomes of various variables, including cancer stage (FIG. 4A), targeted therapy and immunotherapy (FIG. 4B), Framingham Risk Score (FIG. 4C), and smoking history (FIG. 4D). The exemplary results in FIGS. 4A-4B validate many embodiments, as the results are similar to published reports of such studies. In FIG. 4C, the Framingham Risk Score is a cardiac risk score that showed prognostic ability in early and late stage cancers, while not being significant for intermediate stage cancers. Additionally, FIG. 4D shows that smoking history affects survivability in lung cancer, but not in breast cancers.

Individual Prognostics

Figure 5:
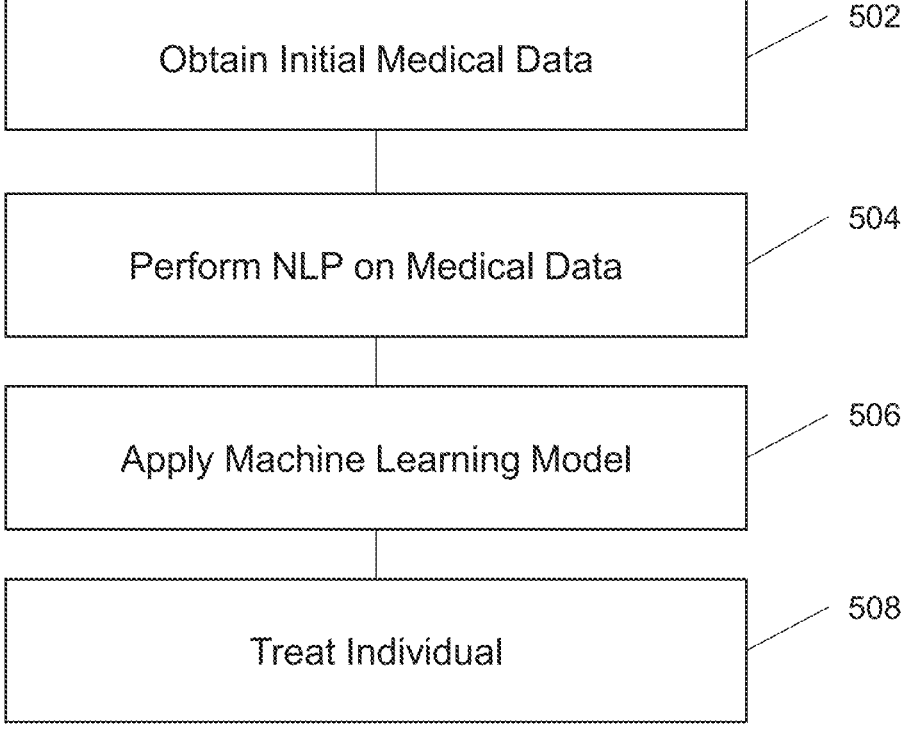
FIG. 5 illustrates an exemplary method of determining a prognosis for an individual in accordance with various embodiments.

Turning to FIG. 5, a method 500 of determining a prognosis for an individual in accordance with many embodiments is illustrated. At 502, various embodiments, obtain initial medical data for an individual. Many embodiments obtain a minimum number of notes for an individual at a specific time point (e.g., 2 weeks after diagnosis, 4 weeks after diagnosis, 30 days after diagnosis, 2 months after diagnosis, etc.).

At 504, many embodiments perform NLP on the obtained notes. As noted above, various embodiments utilize unstructured medical notes for NLP. Many embodiments apply term frequency inverse document frequency (TF-IDF) to identify words that may predict patient survival.

At 506, many embodiments apply a machine learning model trained via NLP data to determine a prognostic for the individual. In certain embodiments, the prognostic is a qualitative and/or quantitative score of severity and/or survivability. For example, some embodiments provide a risk stratum for an individual, while additional embodiments provide a rate of survival over a time period (e.g., 2 years, 5 years, etc.). Additional embodiments identify one or more treatment options for the individual that affect survival prognosis, such as immunotherapy, targeted therapy, radiation therapy, chemotherapy, surgical intervention, and/or any other known treatment for the cancer or tumor.

At 508, many embodiments treat the individual using a treatment identified at 506. Such treatments include immunotherapy, targeted therapy, radiation therapy, chemotherapy, surgical intervention, and/or any other known treatment for the cancer or tumor which increases survival prognosis in the individual.

It should be noted that many embodiments update the prognostics as additional data is obtained for an individual. As such, certain embodiments continually update the medical data for the individual. For example, some embodiments update the medical profile as additional data is generated (e.g., after each office visit, lab, imaging, etc.), while some embodiments update the records on a regular cycle (e.g., every 24 hours, every 7 days, every 30 days, etc.) These embodiments repeat the additional steps 602-608, as additional data is obtained into an embodiment.

Figure 6A:
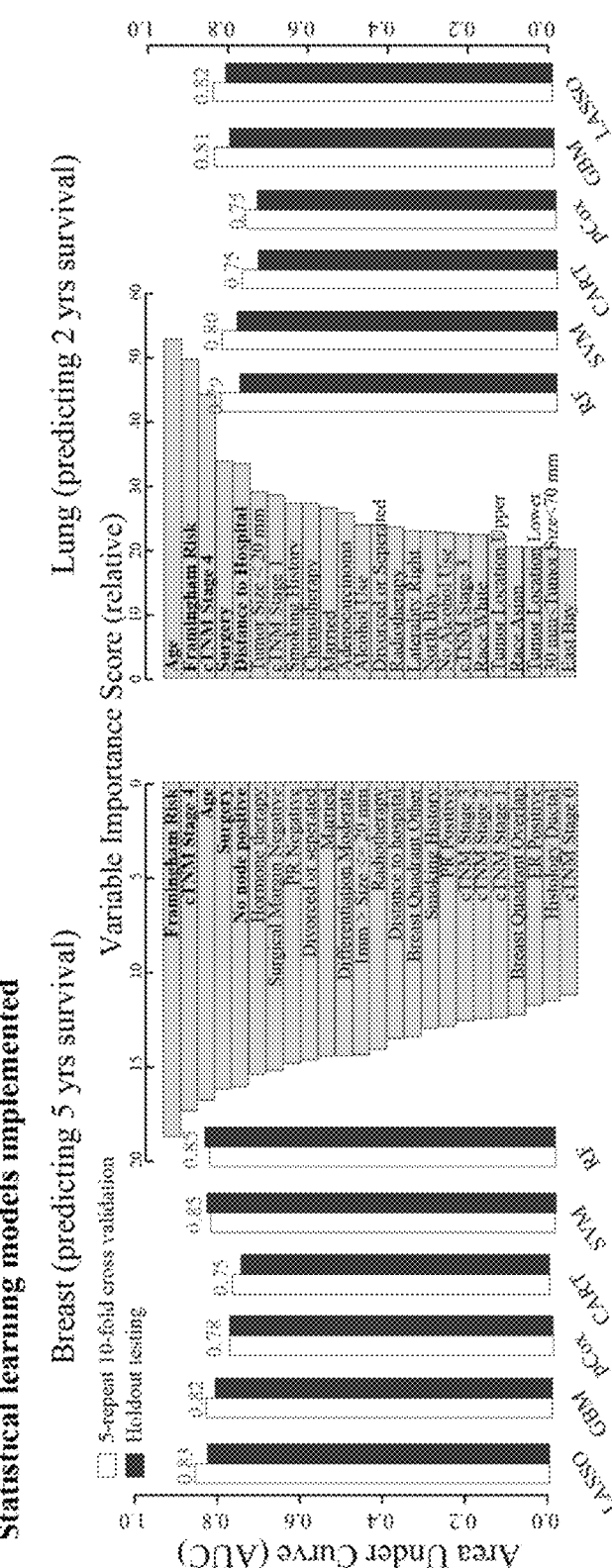
FIGS. 6A-6C illustrate exemplary statistical learning models for prediction of binary survival for breast and lung cancer patients in accordance with various embodiments. Machine learning models created for the binary prediction of patient overall survival using patient selection. Censored patients or patients who were alive with a follow-up less than prediction time points were removed from both training and holdout testing data.
Figure 6B:
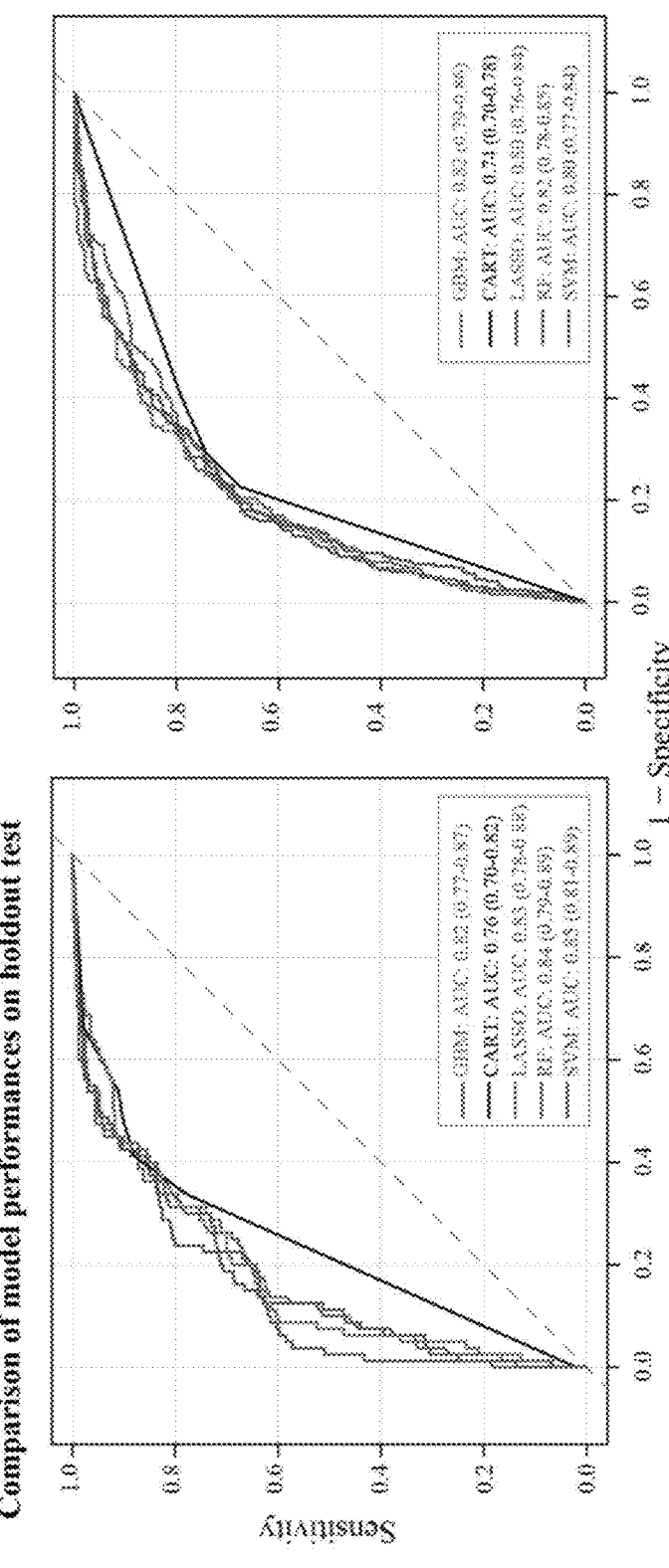
Figure 6C:
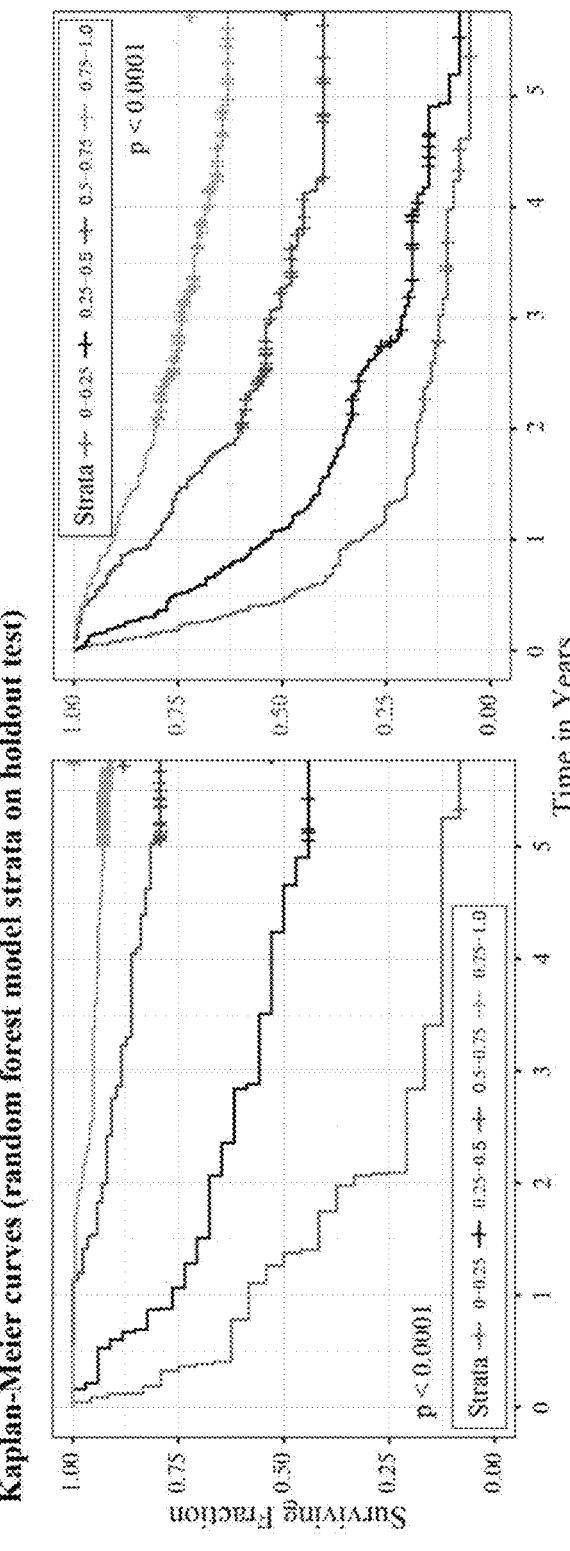

Turning to FIGS. 6A-6C, many embodiments are capable of prognostic analysis of an individual based on medical records and entries for a particular individual. Specifically, FIG. 6A illustrates exemplary data charting area under (AUC) the curve of different machine learning models used in accordance with various embodiments for cross validation and holdout testing data. Additionally, prognostic factors ranked in accordance with importance are illustrated for each of breast and lung cancer. FIG. 6B illustrates exemplary AUC charts for the various models used in various embodiments. FIG. 6C illustrates exemplary risk group stratification for survival prediction in a holdout testing dataset, which provide more defined separations between risk groups as compared to stage alone.

Figure 7:
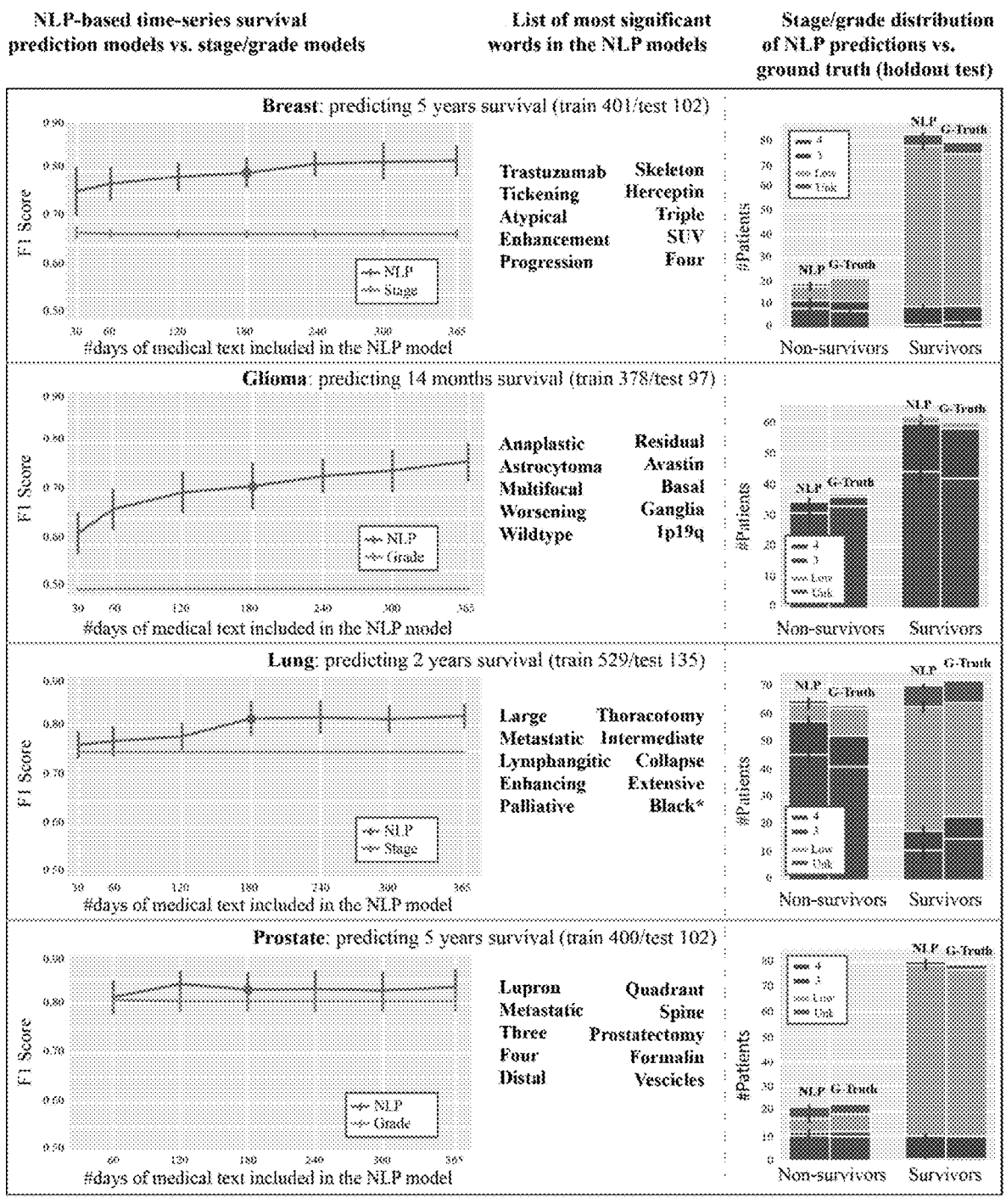
FIG. 7 illustrates an exemplary comparison of natural language processing-based time-series models and stage/grade for prediction of diverse cancer overall survival in accordance with various embodiments, including time series logistic regression of term frequency inverse document frequency (TF-IDF) natural language processing models (21 cross-validation experiments per time point) for the prediction of breast (5 years), glioma (14 months), lung (2 years), and prostate (5 years) binary survival compared to logistic regression models using stage/grade alone. An increasing volume of medical notes from physicians are included in the models for up to 1 year post diagnosis. Error bars indicate the standard deviation of the F1 score performance obtained over 21 experiments for each time point; the ten most important words from the natural language TF-IDF models at 180 days (indicated with the dot) post-diagnosis are presented for each cancer; and a comparison (for stage/grade and age distribution) of the prediction results on the holdout test sets for the selected language models (180 days post diagnosis) versus the ground-truth institutional data for survivors and non-survivors. * The word "black" in the lung cohort was associated with description of gross pathology and not with contextual findings based on ethnicity.

Turning to FIG. 7, many embodiments illustrate improved prognostics for various cancers or tumors over traditional stage or grade systems. Specifically, FIG. 7 illustrates exemplary F1 scores, an exemplary list of significant words that were predictive of survival trajectory, and an exemplary distribution of non-survivor and survivor predictions from embodiments incorporating NLP (NLP) versus ground truth (G-Truth) data for breast cancer, glioma, lung cancer, and prostate tumors. FIG. 7 illustrates that as additional medical data is obtained, the F1 score increases showing improved accuracy as additional data is generated for an individual.

Computer Implemented Embodiments

Figure 8:
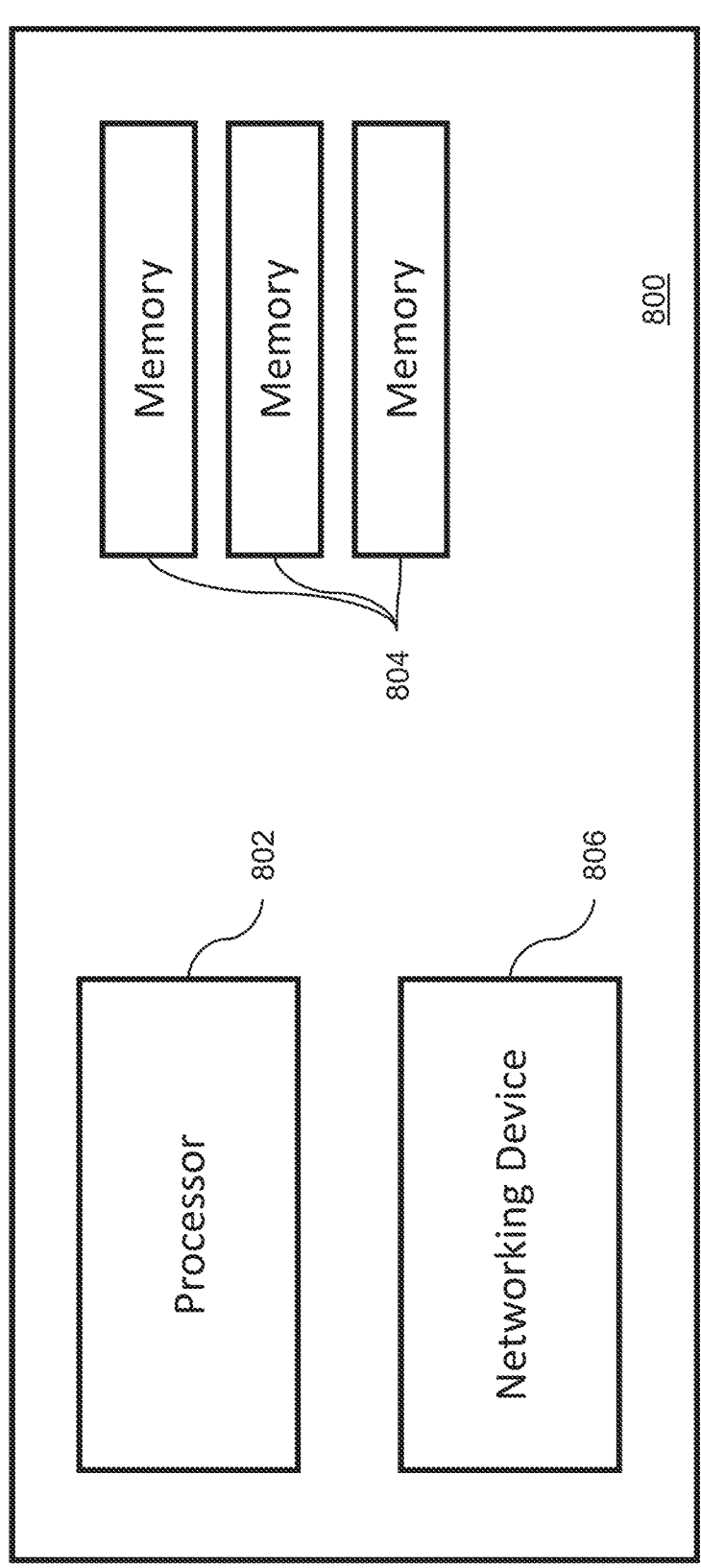
FIG. 8 illustrates a block diagram of components of a processing system in a computing device that can be used in accordance with an embodiment of the invention.

Processes that provide the methods and systems for generating a prognosis in accordance with some embodiments are executed by a computing device or computing system, such as a desktop computer, tablet, mobile device, laptop computer, notebook computer, server system, and/or any other device capable of performing one or more features, functions, methods, and/or steps as described herein. The relevant components in a computing device that can perform the processes in accordance with some embodiments are shown in FIG. 8. One skilled in the art will recognize that computing devices or systems may include other components that are omitted for brevity without departing from described embodiments. A computing device 800 in accordance with such embodiments comprises a processor 802 and at least one memory 804. Memory 804 can be a non-volatile memory and/or a volatile memory, and the processor 802 is a processor, microprocessor, controller, or a combination of processors, microprocessor, and/or controllers that performs instructions stored in memory 804. Such instructions stored in the memory 804, when executed by the processor, can direct the processor, to perform one or more features, functions, methods, and/or steps as described herein. Any input information or data can be stored in the memory 804—either the same memory or another memory. In accordance with various other embodiments, the computing device 800 may have hardware and/or firmware that can include the instructions and/or perform these processes.

Certain embodiments can include a networking device 806 to allow communication (wired, wireless, etc.) to another device, such as through a network, near-field communication, Bluetooth, infrared, radio frequency, and/or any other suitable communication system. Such systems can be beneficial for receiving data, information, or input (e.g., EHR, diagnostic results, imaging, etc.) from another computing device and/or for transmitting data, information, or output (e.g., prognosis) to another device.

Figure 9:
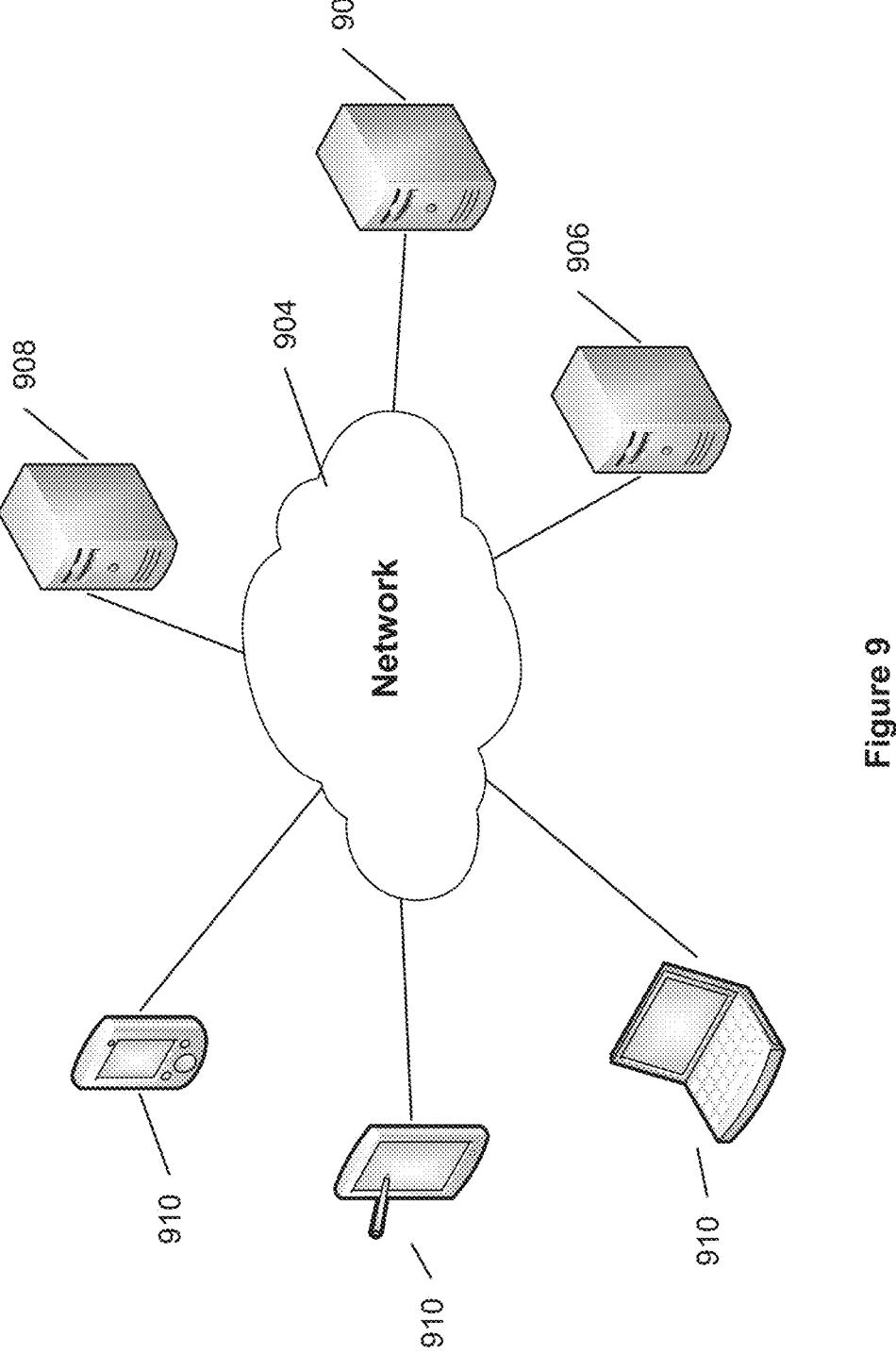
FIG. 9 illustrates a network diagram of a distributed system in accordance with an embodiment of the invention.

Turning to FIG. 9, an embodiment with distributed computing devices is illustrated. Such embodiments may be useful where computing power is not possible at a local level, and a central computing device (e.g., server) performs one or more features, functions, methods, and/or steps described herein. In such embodiments, a computing device 902 (e.g., server) is connected to a network 904 (wired and/or wireless), where it can receive inputs from one or more computing devices, including EHR from a records database or repository 906, diagnostic or imaging data provided from a laboratory computing device 908, and/or any other relevant information from one or more other remote devices 910. Once computing device 902 performs one or more features, functions, methods, and/or steps described herein, any outputs can be transmitted to one or more computing devices 906, 908, 910 for entering into records, taking medical action—including (but not limited to) prehabilitation, delaying surgery, providing antibiotics—and/or any other action relevant to a prognosis. Such actions can be transmitted directly to a medical professional (e.g., via messaging, such as email, SMS, voice/vocal alert) for such action and/or entered into medical records.

In accordance with still other embodiments, the instructions for the processes can be stored in any of a variety of non-transitory computer readable media appropriate to a specific application.

Definitions

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control.

All publications, patents, and patent applications mentioned in this specification are herein incorporated by reference to the same extent as if each individual publication, patent, or patent application was specifically and individually indicated to be incorporated by reference.

It must be noted that, as used in the specification and the appended claims, the singular forms "a," "an," and "the" include plural referents unless the context clearly dictates otherwise.

The terms "subject," "individual," and "patient" are used interchangeably herein to refer to a vertebrate, preferably a mammal, more preferably a human. Mammalian species that provide samples for analysis include canines; felines; equines; bovines; ovines; etc. and primates, particularly humans. Animal models, particularly small mammals, e.g. murine, lagomorpha, etc. can be used for experimental investigations. The methods of the invention can be applied for veterinary purposes. The terms "biomarker," "biomarkers," "marker", "features", or "markers" for the purposes of the invention refer to, without limitation, proteins together with their related metabolites, mutations, variants, polymorphisms, phosphorylation, modifications, fragments, subunits, degradation products, elements, and other analytes or sample-derived measures. Markers can include expression levels of an intracellular protein or extracellular protein. Markers can also include combinations of any one or more of the foregoing measurements, including temporal trends and differences. Broadly used, a marker can also refer to an immune cell subset.

To "analyze" includes determining a set of values associated with a sample by measurement of a marker (such as, e.g., presence or absence of a marker or constituent expression levels) in the sample and comparing the measurement against measurement in a sample or set of samples from the same subject or other control subject(s). The markers of the present teachings can be analyzed by any of various conventional methods known in the art. To "analyze" can include performing a statistical analysis, e.g. normalization of data, determination of statistical significance, determination of statistical correlations, clustering algorithms, and the like.

A "sample" in the context of the present teachings refers to any biological sample that is isolated from a subject, generally a blood or plasma sample, which may comprise circulating immune cells. A sample can include, without limitation, an aliquot of body fluid, plasma, serum, whole blood, PBMC (white blood cells or leucocytes), tissue biopsies, dissociated cells from a tissue sample, a urine sample, a saliva sample, synovial fluid, lymphatic fluid, ascites fluid, and interstitial or extracellular fluid. "Blood sample" can refer to whole blood or a fraction thereof, including blood cells, plasma, serum, white blood cells or leucocytes. Samples can be obtained from a subject by means including but not limited to venipuncture, biopsy, needle aspirate, lavage, scraping, surgical incision, or intervention or other means known in the art.

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored. Similarly, the term "obtaining a dataset associated with a sample" encompasses obtaining a set of data determined from at least one sample. Obtaining a dataset encompasses obtaining a sample, and processing the sample to experimentally determine the data, e.g., via measuring antibody binding, or other methods of quantitating a signaling response. The phrase also encompasses receiving a set of data, e.g., from a third party that has processed the sample to experimentally determine the dataset.

"Measuring" or "measurement" in the context of the present teachings refers to determining the presence, absence, quantity, amount, or effective amount of a substance in a clinical or subject-derived sample, including the presence, absence, or concentration levels of such substances, and/or evaluating the values or categorization of a subject's clinical parameters based on a control, e.g. baseline levels of the marker.

Classification can be made according to predictive modeling methods that set a threshold for determining the probability that a sample belongs to a given class. The probability preferably is at least 50%, or at least 60% or at least 70% or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. Area Under the Curve (AUC) or accuracy, of a particular value, or range of values. In some embodiments, a desired quality threshold is a predictive model that will classify a sample with an accuracy of at least about 0.7, at least about 0.75, at least about 0.8, at least about 0.85, at least about 0.9, at least about 0.95, or higher. As an alternative measure, a desired quality threshold can refer to a predictive model that will classify a sample with an AUC of at least about 0.7, at least about 0.75, at least about 0.8, at least about 0.85, at least about 0.9, or higher.

As is known in the art, the relative sensitivity and specificity of a predictive model can be "tuned" to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about at least about 0.7, at least about 0.75, at least about 0.8, at least about 0.85, at least about 0.9, or higher.

As used herein, the term "theranosis" refers to the use of results obtained from a prognostic or diagnostic method to direct the selection of, maintenance of, or changes to a therapeutic regimen, including but not limited to the choice of one or more therapeutic agents, changes in dose level, changes in dose schedule, changes in mode of administration, and changes in formulation. Diagnostic methods used to inform a theranosis can include any that provides information on the state of a disease, condition, or symptom.

The terms "therapeutic agent", "therapeutic capable agent" or "treatment agent" are used interchangeably and refer to a molecule, compound or any non-pharmacological regimen that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount will vary depending upon the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose will vary depending on the particular agent chosen, the dosing regimen to be followed, whether it is administered in combination with other compounds, timing of administration, the tissue to be imaged, and the physical delivery system in which it is carried.

"Suitable conditions" shall have a meaning dependent on the context in which this term is used. That is, when used in connection with an antibody, the term shall mean conditions that permit an antibody to bind to its corresponding antigen. When used in connection with contacting an agent to a cell, this term shall mean conditions that permit an agent capable of doing so to enter a cell and perform its intended function. In one embodiment, the term "suitable conditions" as used herein means physiological conditions.

EXEMPLARY EMBODIMENTS

Although the following embodiments provide details on certain embodiments of the inventions, it should be understood that these are only exemplary in nature, and are not intended to limit the scope of the invention.

Example 1: Patient Selection

Background: The task of patient selection was approached with the assumption that all EHR systems can suffer from missing data and low data quality. Missing data is a pervasive problem even in a well-designed and controlled study, which arises from incorrectly encoded data, transcription error, item nonresponse, unit non-response, and dropout in follow-up. Although diverse data imputation strategies are often implemented, it was a preference to reduce the number of patients selected in the statistical analysis rather than add artificial data with unclear consequences. Different patient selection approaches were studied.

Methods: Method 1: rely on the cancer registry label which clarifies where (specific institution, hospital and clinics) the patient was diagnosed, treated and followed.

Method 2: augments approach 1 with a study of the volume and continuity of medical entries to select patients with complete medical data.

Method 3: rely exclusively on the distribution of volume and continuity of medical entries to select patients with more complete medical data.

To assess volume and continuity of medical entries, the following was performed: First, for the main cancer populations studied (breast and lung), the number of days in a month with at least one medical entry (notes, medication, encounters, charges, labs, etc.) were calculated beginning six months prior to the initial cancer diagnosis through 24 months post diagnosis. Boxplots were used to inspect the distribution of number of days per month with notes for a given population (FIG. 3A). Using this approach, it became possible to identify patients suspected to only come to the institution for consultation or second opinions. It was also trivial to identify patients lost to follow-up. For the same time period, the total number of days with medical entries was computed. The monthly continuity score (MCS) of entries was computed as:

$$MCS=c*(P-n)/P, \text{ where:}$$

P is the total number of months in the analyzed period,
n is the total number of months without entries,
c is to penalize continuous over non-continuous distribution of months without entries, and has the form: $c=(1+C)/(1+n)$, where C is the total number of continuous segments of months without entries in the analyzed period.

Scatter plots were used (FIG. 3B) to investigate possible clusters of total number of days with medical entries versus the MCS score. Simple threshold in data volume and MCS score using clustering (quantile values) were investigated to select patients for statistical learning.

Finally, the accumulated MEDomics features of the remaining patients were evaluated for their data completeness. MEDomics features with at least 60% completeness amongst the cancer group were automatically kept for further analysis. Final statistical learning was performed with careful selection of patients given the completeness of features.

Results: Because oncologic care necessitates regular and frequent follow up and interventions, particularly within the initial period following diagnosis, simple patient selection approaches were tested prior to statistical learning (Table 2). One pragmatic approach is to select patients based on adequate distribution of volume and continuity of clinical care. For example, following a diagnosis of breast cancer, the maximum number of days of different medical entry types (medical notes, encounters, labs, etc.) in a given month ranges between 2 and 8 for the first 1-2 months after diagnosis, and gradually decreases over 2 years (FIG. 3A). To identify a threshold for patient selection, we calculated a penalized continuity score of medical entries as well as the total number of days with entries (FIG. 3B); we then validated the ability of these two metrics to distinguish between patients presenting for a second opinion and receiving the majority of their care elsewhere (i.e. partial care), versus patients receiving their complete care at our institution as determined using the regional cancer registry label. FIG. 3B demonstrates the ability of the entry volume and continuity score to identify patients for inclusion (dots/circles) or exclusion (Xs) from further statistical analysis. Ultimately, we selected patients with high-quality data defined as high-volume, high-continuity, and highly complete feature set (FIGS. 3A-3C), for further development of statistical models. These included 3782 breast and 2054 lung cancer patients for the primary statistical analysis. The lists of extracted MEDomics features and outcomes for these two cancers are available for three different patient selection methods in Tables 3 and 4. A statistical analysis of possible patient selection bias (Tables 5 and 6) demonstrated that excluded patients had a higher percentage of missing values (in staging, site primary, tumor size, differentiation, etc.), tended to live further away from the institution and had differences in some of the calculated features such as the Framingham risk score. The excluded patients also had a higher percentage of deaths compared to our selected cohorts. There were only small differences between the cohorts selected for analysis (Tables 3-6) for both breast and lung cancer prior to performing statistical learning.

Example 2: Exploration of Regional Patterns of Care

Methods: The MEDomics table (immunotherapy) and problem list (ICD code) tables to explore the cancer care patterns (surgery, radiation and immunotherapy) of the institution in the San Francisco Bay Area for the years 2014-2019. The distribution of cases per year per region was plotted for urology, digestive, breast, neurology, bone, head and neck, and thoracic cancers.

Figure 10:
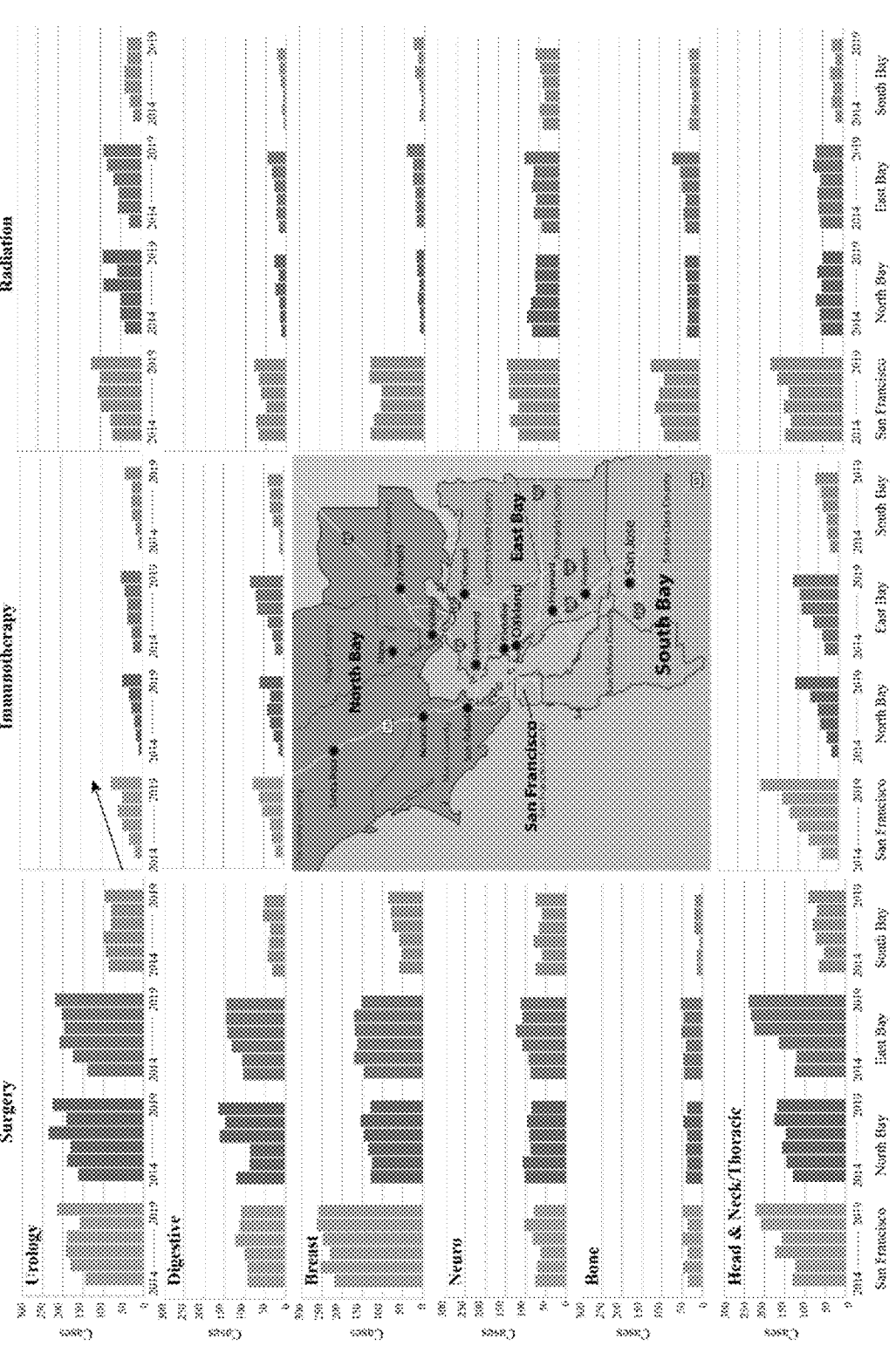
FIG. 10 illustrates an exemplary exploration of regional oncology patterns of care in accordance with various embodiments. Left column—Number of new cancer cases treated with surgery per year (2014-2019) per region (San Francisco, North Bay, East Bay and South Bay). Middle column—Number of cancer patients receiving immunotherapy medication per year per region. Right column— Number of new cancer cases treated with radiation per year per region.

Results: Capitalizing on the MEDomics data structure, an analysis of institutional regional patterns of care was performed for diverse cancers and plotted in the San Francisco Bay area map for the last 5 years (FIG. 10). The general trends in patients treated (surgery, radiation and immunotherapy) at the institution in the last 5 years can be observed in institutional regional care patterns. In total, the number of cancer patients treated at the institution in the last 5 years increased by an average of 18%. The number of thoracic and head and neck cancer patients treated with surgery nearly doubled over that time period. Of this cohort, an increasing number of patients received immunotherapy (from ~50 cases in 2014 to ~200 cases in 2019 for the San Francisco region alone). For neuro-oncological diseases, patients from outside San Francisco visit our institution for surgery and radiation treatment, due to its presence as a center of expertise. However, most of the patients that receive radiation treatment for breast cancer are from San Francisco, as patients elsewhere may tend to seek treatment closer to home. The ability to explore these care patterns and regional trends in a "management dashboard" may become important to study additional sources of bias in the data.

Example 3: In Silico Clinical Trials

Background: A group of six oncology experts were asked to identify research questions that a) concern clinically relevant issues, b) have not been fully answered in clinical trials, c) could be evaluated using data obtained during routine care, and d) could affect current clinical practice. The cardio-vascular risk and smoking status were selected to study the effect on diverse cancer patient survival.

These questions were approached using a digital twin or in silico randomized trial approach. In short, clusters were defined of similar patients based on multivariate analysis. For each patient of interest, a control patient arm was randomly chosen from the same cluster. For example, for a cancer patient A that was treated with immunotherapy, it was attempted to find a similar control patient B that was treated during the same period, but did not receive immunotherapy. It was ensured that all the patients in the treatment and control groups were unique. The survival of the group was then compared with immunotherapy and the control group without immunotherapy.

In silico trials for lung and breast cancer cohorts were conducted using the following variables:
Disease staging: this served as a positive control, with a clear effect. Astrological zodiac sign: this served as a negative control, with no expected effect.

Prescription of targeted drugs (Olaparib, Trastuzumab, Pertuzumab, Lapatinib, Neratinib, Palbociclib, Talazoparib, Ribociclib, Abemaciclib, Alpelisib) for stage 4 breast cancer.

Prescription of immunotherapy drugs (Ipilimumab, Nivolumab, Pembrolizumab, Atezolizumab, Avelumab, Duralumab) for stage 4 lung cancer.

Framingham risk score for the breast and lung data stratified by stage.

Patient smoking history (current or former smokers vs never smokers) stratified by stage.

Figure 11:
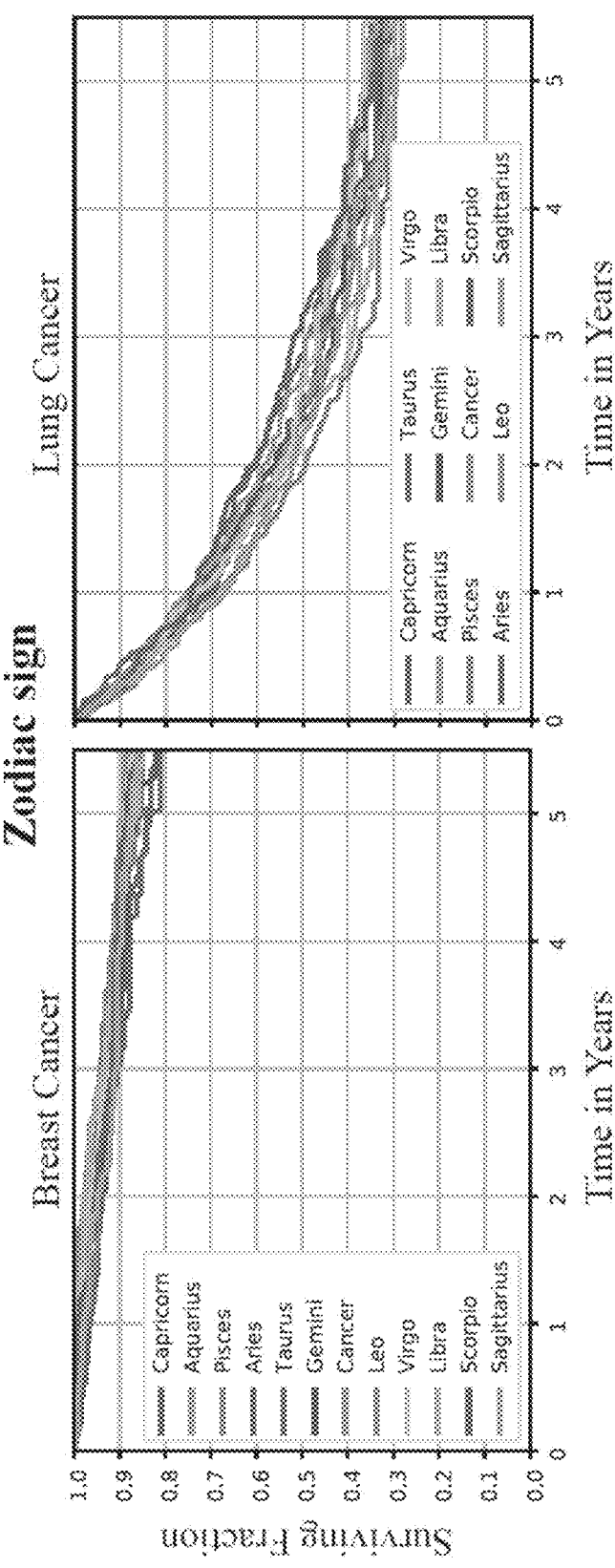
FIG. 11 illustrates exemplary Kaplan-Meier survival plots on breast and lung cancer patients stratified by zodiac sign in accordance with various embodiments. Comparison of Kaplan-Meier survival plots for breast and lung patients stratified astrological zodiac sign as a negative control.

Kaplan-Meier estimates were plotted to visualize the probabilities of overall survival for each of the investigated variables. The difference between risk strata was assessed using the hazard ratio, 95% confidence interval and log-rank tests. Tests with p-value <0.05 were considered to be statistically significant Results: The effect of clinical stage on breast and lung cancer patient survival is presented in FIG. 4A. These survival estimates appeared consistent (within 95% confidence interval) with published literature. As a negative control, patients were stratified by astrological zodiac sign after balancing the group for staging (FIG. 11). For the studied cancer groups, there were no statistically significant differences (logrank test, p>0.05) in survival between the astrological signs.

The ability of the approach to recapitulate known prognosticators was further tested in breast and lung cancer. The effects of targeted therapy and immunotherapy on mortality in metastatic breast and lung cancer were examined (FIG. 4B). It was found that hormone receptor targeted therapy was statistically significantly correlated with improved overall survival in stage IV breast cancer patients; the magnitude of these effects appeared consistent (within 95% confidence interval) to previously reported clinical trial results. In addition, it was found that use of immunotherapy was statistically significantly correlated with improved overall survival among stage IV lung cancer patients, again with a magnitude consistent (within 95% confidence interval) with published trial results.

It was also wished to test whether known comorbidities and clinical risk-stratification tools would be found to have prognostic significance within the MEDomics context. Cardiac morbidity has previously been associated with overall survival, either as a competing risk or negatively correlating with oncologic outcomes. MEDomics was utilized to compute and apply a widely known cardiovascular risk score, the Framingham risk score, (FIG. 4C), with the hypothesis that cardiovascular risk may be prognostic for overall mortality in our cohort of oncology patients. For breast cancer, the Framingham risk score was significantly prognostic for patient survival among early and late-stage patients but did not reach significance for intermediate stage patients. For lung cancer patients, the Framingham risk score was similarly prognostic for patient survival among early and late-stage patients and likewise did not reach significance among patients with intermediate stage. This is the first known time the Framingham score has been directly related to overall survival in a large dataset of real-world oncology patients.

Finally, the impact of current or prior smoking was examined on mortality in a cohort (FIG. 4D). For breast patients, smoking had no significant association with survival in patients of all stages of the disease. However, smoking was significantly associated with increased mortality among all stages of lung cancer patients.

Example 4: Machine Learning for Overall Survival

Methods: Multifactorial models were built to identify patients with overall survival (OS) above or below 5 years for breast cancer and 2 years for lung cancer. Prior to model training, lung and breast cancer patient cohorts were each split into a training (67%) and a test (33%) set using stratified sampling (Table 2, method 1 (see Example 2)) and a split based on time of diagnosis (Table 2, method 2 & 3 (see Example 2)). A univariate analysis of clinical features was performed using a Cox proportional-hazards model on the training cohort. Subsequently features which were significant (p<0.05) were used for the multivariate penalized-Cox (pCox) proportional-hazards analysis. Various ML algorithms such as Support Vector Machine (SVM), Random Forest (RF), Classification and Regression Tree (CART), logistic regression with elastic net regularization (GLMNET), least absolute shrinkage and selection operator (LASSO), and Gradient Boosting Machines (GBM) were implemented for prediction of binarized survival endpoints. These algorithms were chosen as these are commonly used algorithms in medicine and well suited for structured data. All models presented in the manuscript were trained using ten-fold cross-validation that was repeated five times. Model performance was assessed in the separate holdout test set. For consistency reasons, all algorithms used the same samples within the training and validation folds during cross-validation and for holdout testing. Hyperparameters of each algorithm were tuned using grid search. Adjustment for imbalanced classes was done using SMOTE during cross-validation steps. For each algorithm, a final combination of variables was determined based on the highest cross-validation AUC following step-wise feature selection guided by ranked feature using feature importance. The performance of all the ML algorithms was assessed by calculating various metrics (AUC and balanced accuracy) across the training set and 5-repeat 10-fold cross-validation and test sets. The entire analysis was implemented and carried out in R (version 3.6.1; R Foundation for Statistical Computing, Vienna, Austria) using Caret package.

Natural Language Processing: The objective of this analysis was to study possible insights about performing n-year cancer survival prediction using unstructured medical text notes. Patients with breast (5 years), glioma (1.17 years), lung (2 years) and prostate cancer (5 years) were selected. Each cancer type was treated as a separate study but followed the same methodology. For patients in the cancer registry, all notes from physicians were selected; i.e. regular notes, all narrative and impression notes from radiology reports and all impression notes from pathology reports. All notes were de-identified using the clinical text de-identification software PHIlter to remove protected health information (PHI) and possible institutional biases (names of institution, department or physicians) from plain text. All code was implemented and tested using Python 3.7.4. and the packages: sklearn 0.21.3, imblearn 0.4.3.

With $t_0=0$ set as the diagnosis day, a time series of a number of days after diagnosis $(t_1, t_2, t_3, \ldots)$ was defined. At time $t_1$, a fixed patient cohort was selected that was used in all experiments, as follows: only patients with more than three notes between to and $t_1$ were included (Table 2, method 4 (see Example 2)). Subsequently, these patients were randomly assigned to the training or test sets with a 4:1 size ratio (Tables 11-12). This assignment was performed in a nested stratified fashion that preserved the proportion of samples for each stage/grade and survival. The random assignment was repeated twenty-one times.

At each time point in the time series, the available de-identified text notes aggregated up to that time point was collected. These notes were then tokenized as a collection of terms using white spaces as token separators, and the term frequency inverse document frequency (TF-IDF) was computed to use as semantic features. Then, the minority classes were randomly over-sampled on the training set to address class imbalance for survival. Subsequently, identified optimal hyperparameters for fitting a regularized logistic regression model through a grid search using stratified five-fold cross validation. A logistic regression model was then fit with these hyperparameters and used to prognosticate overall survival in the test set. We then computed the F1 score from the predicted classes. This procedure was repeated for each of the twenty-one random splits. Afterwards, computed the mean and standard deviation of the F1 score was computed for the specific time point. For comparison, we used disease stage or grade data at baseline ($t_0$) using the sample statistical procedure as described above.

The meta-transformer implemented in the function SelectFromModel method from the scikit-learn package was used along with the logistic regression models to select the 200 most important terms based on coefficient weights for each time point $t_1$. These were then aggregated at 180 days post-diagnosis over the twenty-one splits by computing the occurrence rate. The ten most important terms were eventually selected to be presented in FIG. 7.

Results: After setting apart 33% of the patients in each cohort as a separate holdout test set (Table 2, method 1 (see Example 2)), the remaining patients were used to first systematically identify variables that are related to overall survival. A univariate Cox analysis showed that, in addition to known factors such as stage, age, and tumor size, the Framingham risk score (p-value<0.001) and marital status (p<0.001) were also associated with survival of breast cancer patients (Table 7). For the lung cohort, similar established factors were found, but Framingham risk score and marital status were not significantly associated with survival on univariate analysis (Table 8).

Figure 12:
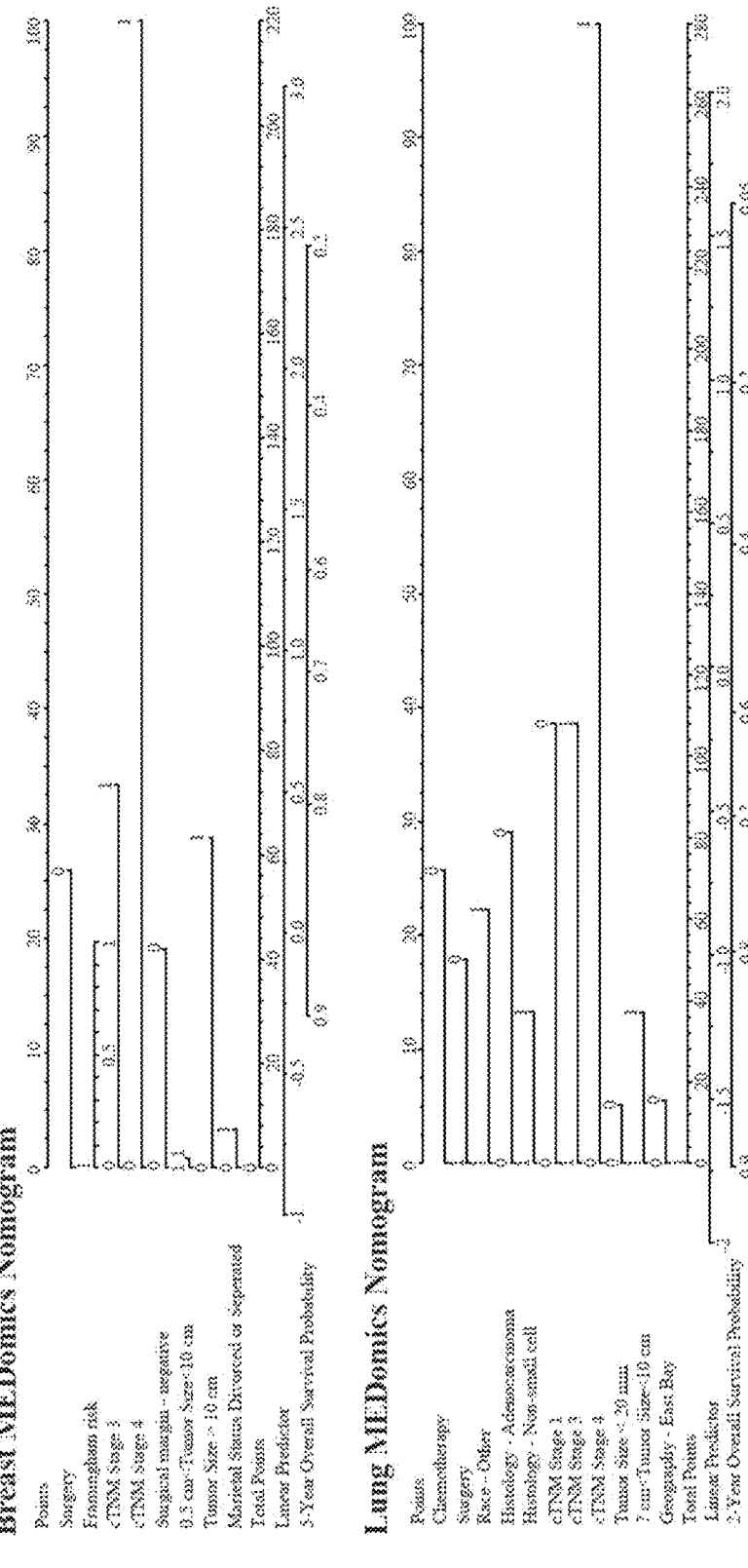
FIG. 12 illustrates exemplary breast and lung cancer survival nomograms in accordance with various embodiments. Nomograms built using penalized Cox regressions for determination of the probability of breast (5 years) and lung (2 years) overall survival.

Nomograms were subsequently created to estimate mortality (FIG. 12). Including the Framingham risk score in the breast cancer nomogram improved discrimination between patients for five-year mortality with an area under the receiver operating characteristic curve (AUC) of 0.78 (95% confidence interval CI 0.74-0.82) compared to 0.73 (95% CI 0.68-0.77) for the baseline in the holdout test set. Both the Framingham risk score and marital status played a significant role in the breast nomograms.

Six different ML algorithms were compared to prognosticate mortality. All algorithms could discriminate well between patients with short and long survival (FIGS. 6A-6B) in both internal cross-validation and the holdout test set. The AUC varied between 0.75 (95% CI 0.69-0.81) and 0.85 (95% CI 0.80-0.90) for breast cancer in the holdout test set. For lung cancer the AUC varied between 0.75 (95% CI 0.71-0.76) and 0.82 (95% CI 0.78-0.85).

A permutation test was used to assess variable importance in the random forest model (FIG. 6A). This revealed that established prognostic factors such age, high staging, and the provided treatment were indeed important for both cancer types. Other less well-known factors such as the Framingham risk score, distance to hospital and marital status also ranked high in importance. All classifiers performed well (FIG. 6B) with the MEDomics features provided in the holdout test set.

Figure 13A:
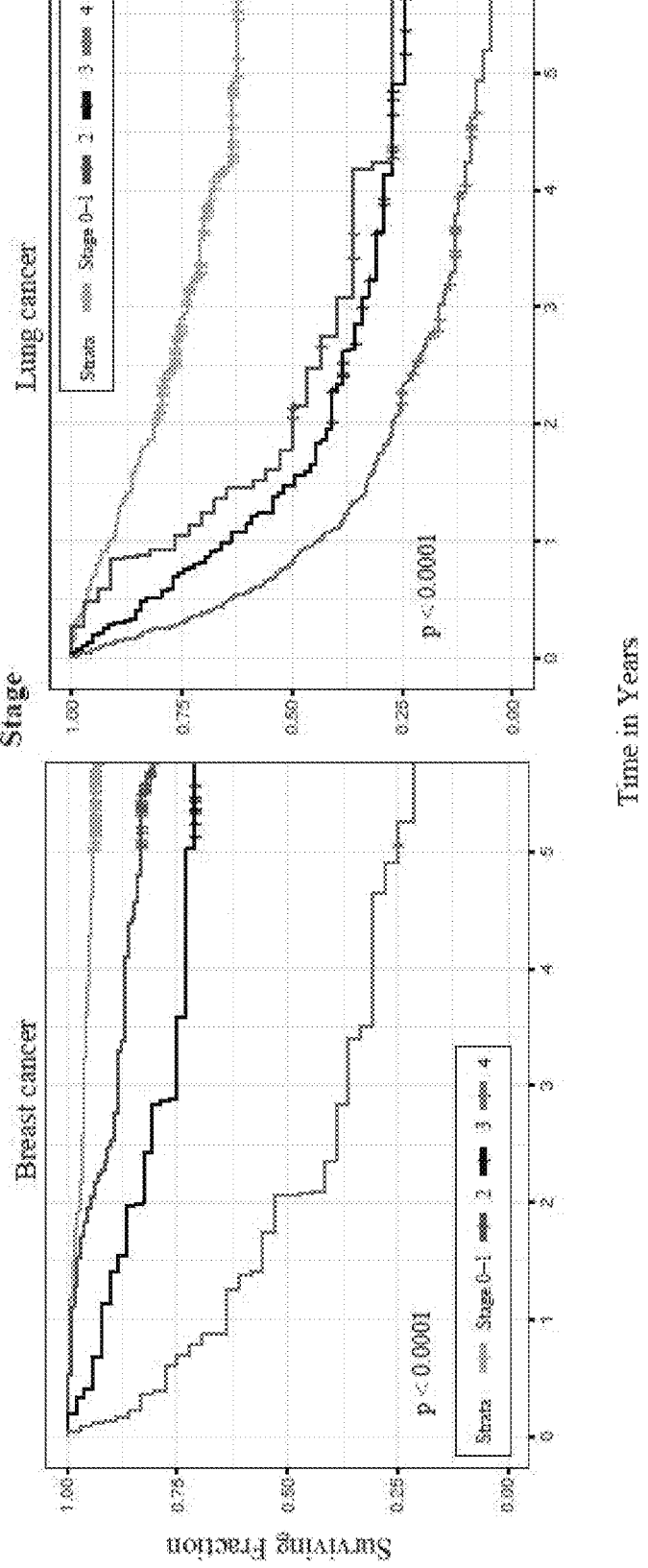
FIGS. 13A-13B illustrate exemplary Kaplan-Meier survival plots on breast and lung cancer patients in accordance with various embodiments. Comparison of Kaplan-Meier survival plots for breast and lung patients stratified by FIG. 13A. stage and FIG. 13B. machine learning strata using the random forest predictions with patient selection and data split.
Figure 13B:
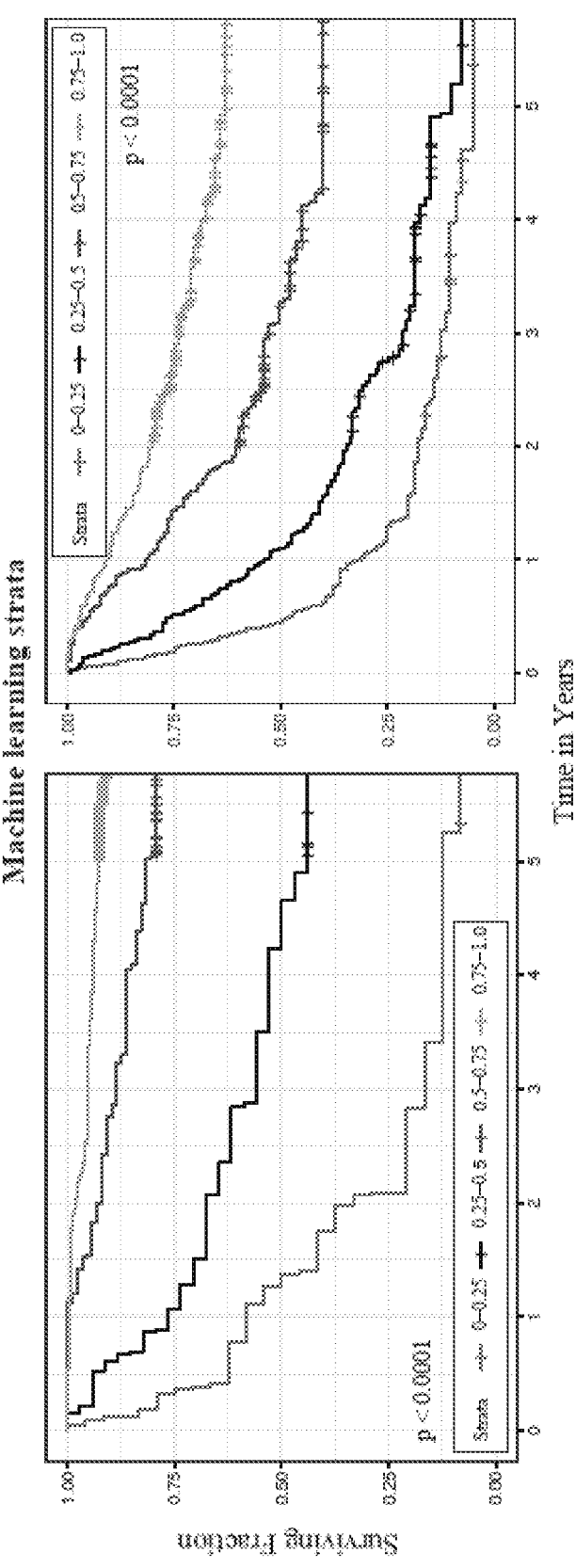
Figure 14A:
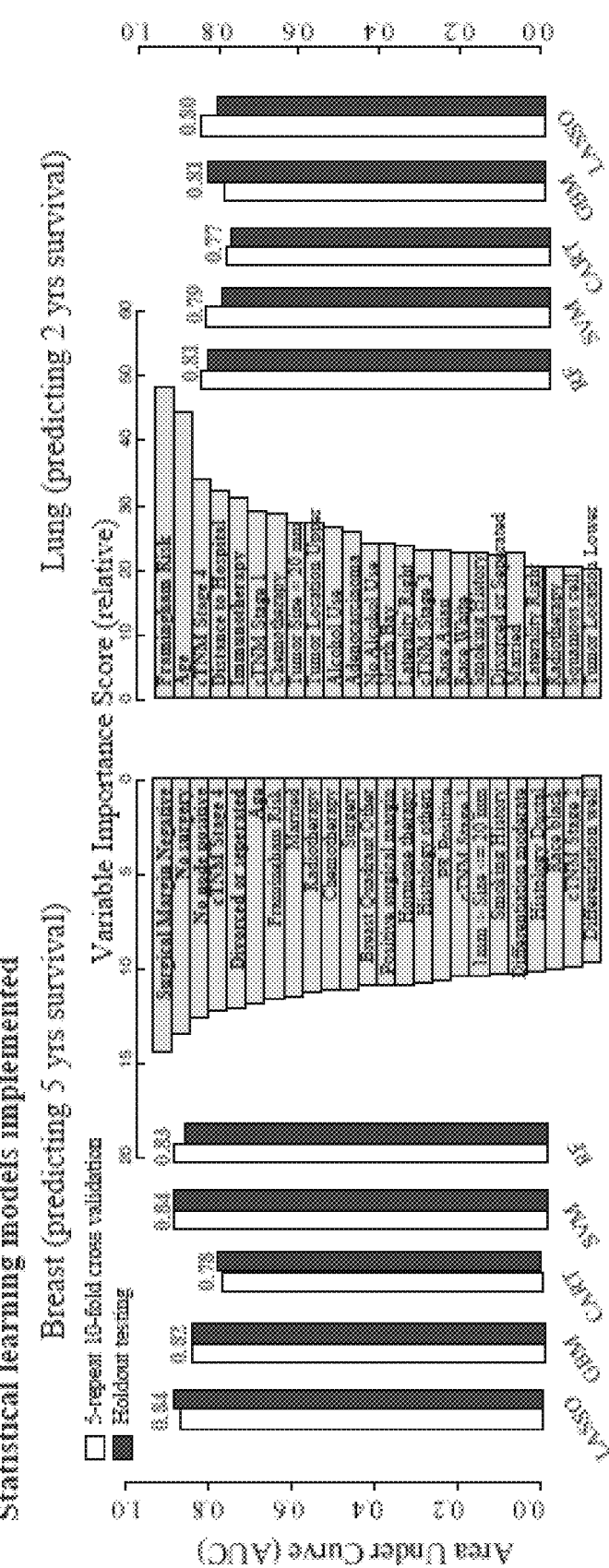
FIGS. 14A-14C illustrate exemplary statistical learning models for prediction of binary survival for breast and lung cancer patients (data split based on time) in accordance with various embodiments. Machine learning models created for the binary prediction of patient overall survival using patient selection and data split. Censored patients or patients who were alive with a follow-up less than prediction time points were removed from both training and holdout testing data.
Figure 14B:
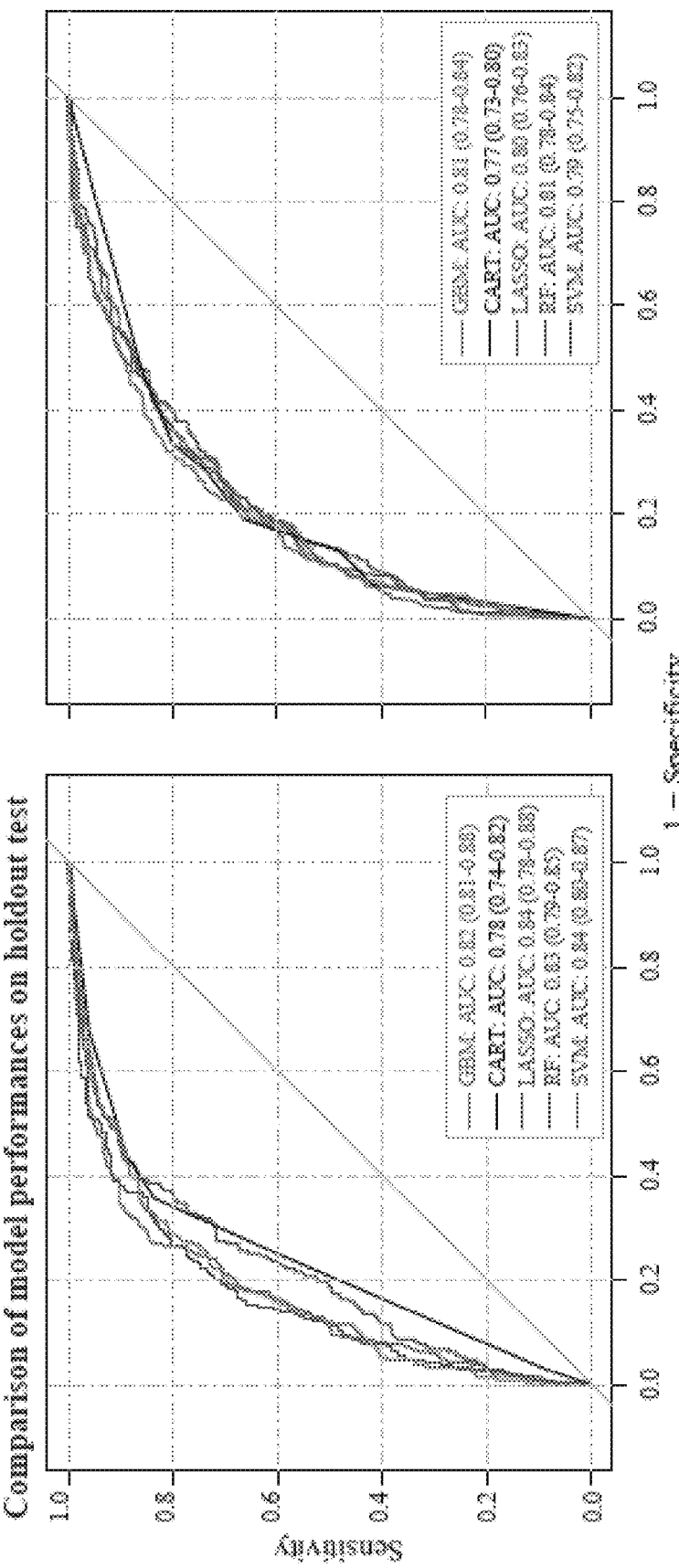
Figure 14C:
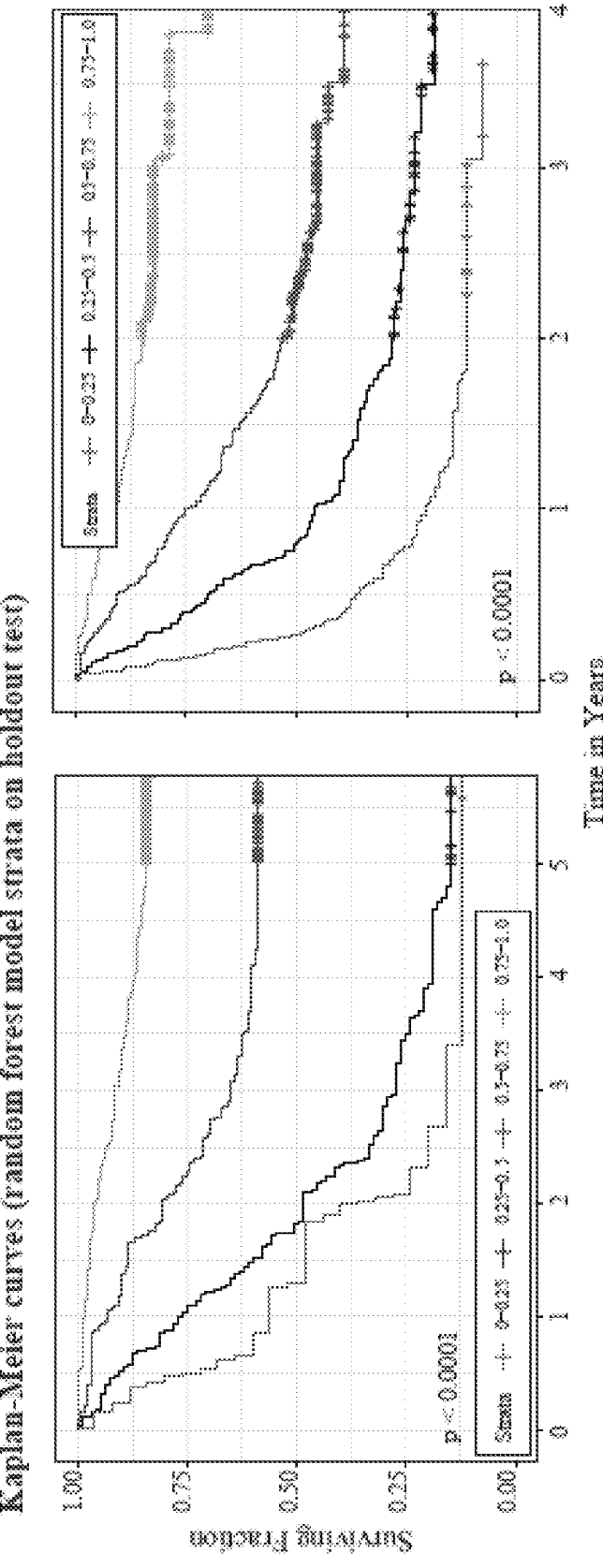
Figure 15A:
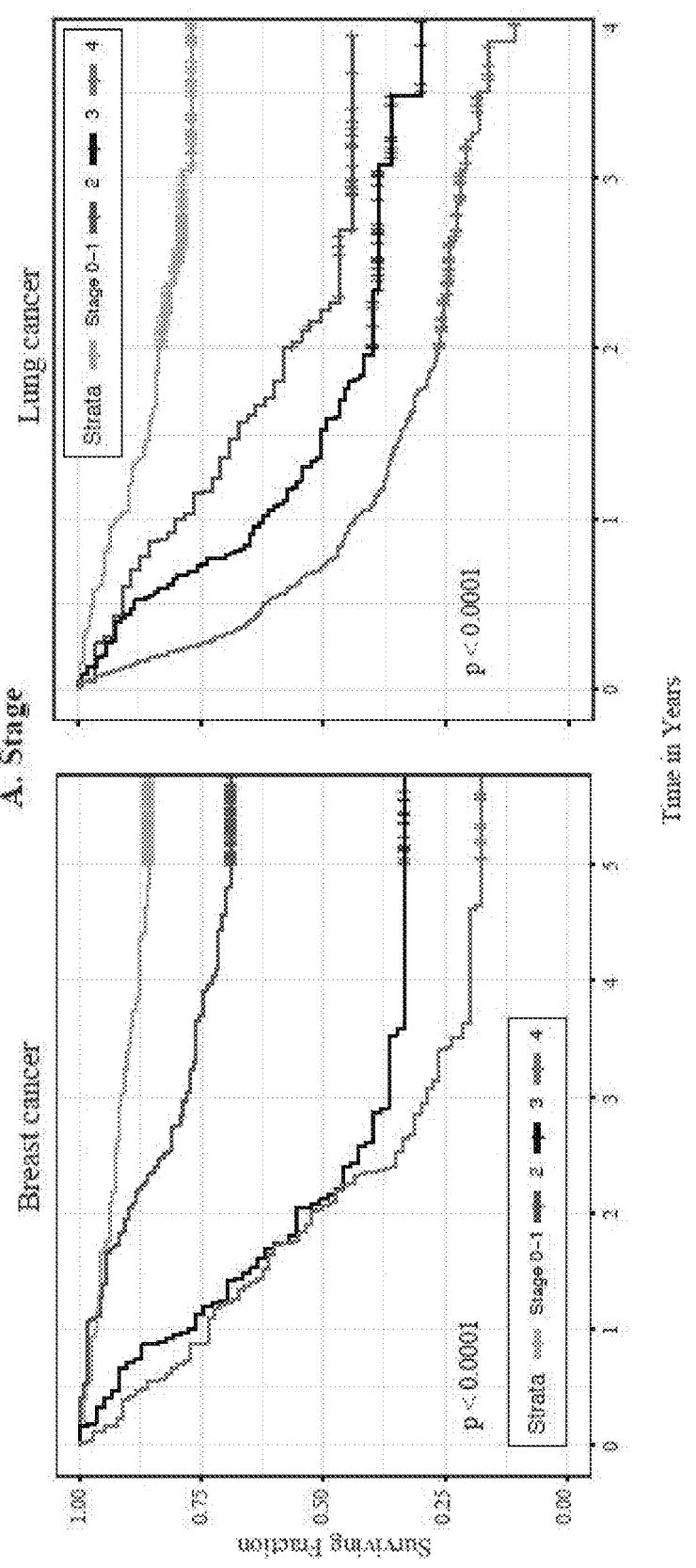
FIGS. 15A-15B illustrate exemplary Kaplan-Meier survival plots on breast and lung cancer patients (data split based on time) in accordance with various embodiments. Comparison of Kaplan-Meier survival plots for breast and lung patients stratified by FIG. 15A. stage and FIG. 15B. machine learning strata using the random forest predictions with patient selection and data split.
Figure 15B:
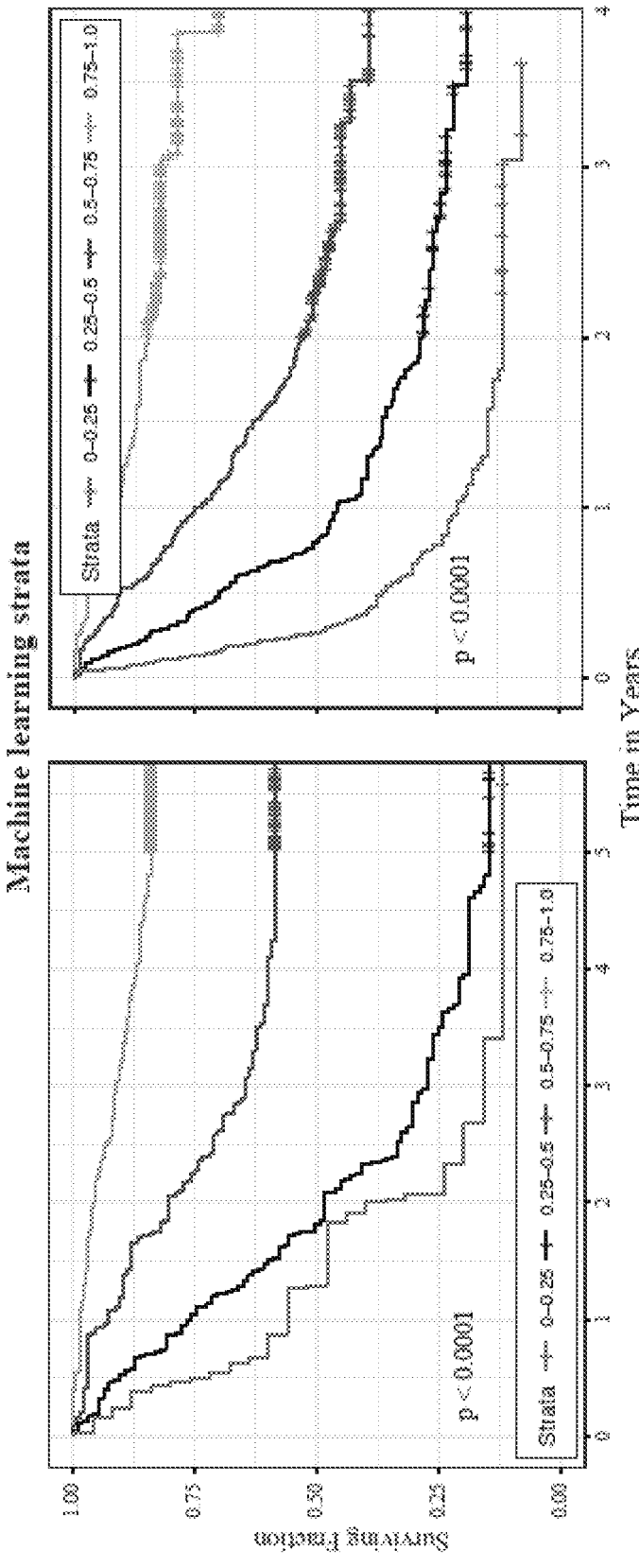

Patients were then stratified from the test set into four risk groups based on the cumulative hazards predicted by the random forest models. The resulting stratification is shown using Kaplan-Meier plots (FIG. 6C). Significant differences in overall survival were observed (between all groups individually) for both cohorts (p<0.001). These ML based strata resulted in more defined separations between risk groups compared to using stage alone (FIGS. 13A-13B).

Finally, ML models were built using time of diagnosis for splitting the training and testing sets and using different patient selection methods (Table 2, methods 2 and 3 (see Example 2)). These additional analyses provided consistent results (FIGS. 14A-14C, FIGS. 15A-15B, and Table 3). Ultimately, all patient selection methods and data split strategies (random stratified and time-based) lead to similar performance across the cancer types studied and ML algorithms (Tables 9 and 10). These proof-of-principle results require further validation but support the hypothesis that clinically relevant ML is possible from real-world data.

In order to capitalize on the large volume of unstructured medical text available in the MEDomics database, a simple NLP methodology was applied using term frequency inverse document frequency (TF-IDF) to predict patient survival. A minimum requirement on the number of medical notes at 30 days after diagnosis was used for patient selection (Table 2, method 4 (see Example 2)) of the NLP cohorts (Tables 11-12). As a patient's illness course unfolded, new physician notes were incorporated into the NLP model. These time-series NLP models (FIG. 7) were compared to static logistic regression models of survival based on traditional clinical stage (breast and lung) or tumor grade (glioma and prostate). For all cancers, the NLP model progressively improved in accuracy as more medical text was included over time. For breast cancer, the NLP model outperformed staging by 10 to 24% (average F1 score of 0.80 compared to 0.67). For glioma, the NLP model outperformed staging in F1 score by 10 to 40% (average F1 score of 0.72 versus 0.55). For lung, the NLP models increasingly outperformed staging in F1 score after 4 months of medical notes post diagnosis. For prostate cancer, the NLP model performances were only marginally superior than grade, perhaps owing to the relatively low 5-year mortality and long disease trajectory among patients with prostate cancer. The NLP models identify the appearance of key cancer specific words predictive of survival trajectory (FIG. 7). Finally, the NLP models applied to the holdout test set resulted in consistent stage/grade distributions compared to the ground-truth in the survivor and non-survivor groups (FIG. 7).

DOCTRINE OF EQUIVALENTS

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the foregoing examples and descriptions of various preferred embodiments of the present invention are merely illustrative of the invention as a whole, and that variations in the components or steps of the present invention may be made within the spirit and scope of the invention. Accordingly, the present invention is not limited to the specific embodiments described herein, but, rather, is defined by the scope of the appended claims.

What is claimed is:

1. A method for determining cancer prognosis, comprising:

obtaining, by a server, medical data for an individual from a medical records database, wherein the medical data comprises physician notes;

performing natural language processing (NLP) on the medical data by:

extracting, by the server, a plurality of tokens from the medical data using a feature extraction model that breaks the physician notes into tokens of sub-word units, wherein each of the plurality of tokens comprises one or more of: a token embedding, a segment embedding that identifies a sequence the token embedding associates with, and a positional embedding comprising a position of the token in the physician notes;

applying, by the server, term frequency inverse document frequency (TF-IDF) to the extracted tokens;

in response to applying the TF-IDF, identifying, by the server, a set of key terms that predict cancer survivability, wherein each of the set of key terms includes a set of one or more extracted tokens; and generating, by the server, a conditional latent space as a multi-dimensional vector from a final hidden layer of the feature extraction model using the sets of one or more extracted tokens from the identified set of key terms;

determining, by the server, at least one prognostic for the individual by applying a machine learning model on the generated conditional latent space to determine a prognostic for the individual;

identifying, by the server, at least one treatment option for the individual based on the prognostic for the individual, wherein the at least one treatment option is selected from immunotherapy, targeted therapy, radiation therapy, chemotherapy, and surgical intervention;

transmitting, by the server, the at least one treatment option to one or more devices associated with a physician; and in response to the transmitting, administering the individual with the at least one treatment option.

2. The method of claim 1, wherein the machine learning model identifies a treatment option for the individual, wherein the treatment increases the prognostic for the individual.

3. The method of claim 2, further comprising treating the individual with the identified treatment to increase the prognostic for the individual.

4. The method of claim 1, further comprising updating the medical data for the individual.

5. The method of claim 4, further comprising:

performing NLP on the updated medical data; and re-applying the machine learning model on the updated natural language processed medical data to update the prognostic for the individual.

6. The method of claim 1, wherein the machine learning model is trained by:

obtaining a collection of medical records from a medical institution, wherein each record in the collection of medical records comprises data for an individual diagnosed with cancer;

processing the collection of medical records; and performing NLP on the collection of medical records.

7. The method of claim 6, wherein the processing comprises de-identifying the collection of medical records.

8. The method of claim 6, wherein the processing comprises separating the records for a single cancer type.

9. The method of claim 6, further comprising selecting complete records in the collection of medical records.

10. The method of claim 1, wherein the machine learning model is selected from a Support Vector Machine (SVM), a Random Forest (RF), a Classification and Regression Tree (CART), a logistic regression with elastic net regularization (GLMNET), a least absolute shrinkage and selection operator (LASSO), and a Gradient Boosting Machines (GBM).

11. A system for determining a cancer prognosis for an individual, comprising:

one or more processors;

a memory readable by the one or more processors;

a network interface;

instructions in the memory that when read by a processor configures the processor to:

obtain medical data for an individual from a medical records database, wherein the medical data comprises physician notes;

perform natural language processing (NLP) on the medical data by:

extracting a plurality of tokens from the physician notes using a feature extraction model that breaks the physician notes into tokens of sub-word units, wherein each of the plurality of tokens comprises one or more of: a token embedding, a segment embedding that identifies a sequence the token embedding associates with, and a positional embedding comprising a position of the token in the physician notes;

applying term frequency inverse document frequency (TF-IDF) to the extracted tokens;

in response to applying the TF-IDF, identify a set of key terms that predict cancer survivability, wherein each of the set of key terms includes a set of one or more extracted tokens;

generating a conditional latent space as a multi-dimensional vector from a final hidden layer of the feature extraction model using the sets of one or more extracted tokens from the identified set of key terms;

determining at least one prognostic for the individual by applying a machine learning model on the generated conditional latent space to determine a prognostic for the individual;

identifying at least one treatment option for the individual based on the prognostic for the individual, wherein the at least one treatment option is selected from immunotherapy, targeted therapy, radiation therapy, chemotherapy, and surgical intervention;

transmitting the at least one treatment option to one or more devices associated with a physician; and in response to the transmitting, administering the individual with the at least one treatment option.

12. The system of claim 11, wherein the machine learning model is trained by:

obtaining a collection of medical records from a medical institution, wherein each record in the collection of medical records comprises data for an individual diagnosed with cancer;

processing the collection of medical records; and performing natural language processing (NLP) on the collection of medical records.

13. The system of claim 12, wherein the processing comprises de-identifying the collection of medical records.

14. The system of claim 12, wherein the processing comprises separating the records for a single cancer type.

15. The system of claim 12, further comprising selecting complete records in the collection of medical records.

16. The system of claim 11, wherein the system is configured to receive electronic health records from a plurality of medical institutions.

17. The system of claim 16, wherein the system is configured to receive the electronic health records via a network through the network interface.

\* \* \* \* \*